(12) United States Patent
Anderson et al.

(10) Patent No.: US 8,034,369 B2
(45) Date of Patent: *Oct. 11, 2011

(54) CONTROLLED RELEASE BIOACTIVE AGENT DELIVERY DEVICE

(75) Inventors: Aron B. Anderson, Minnetonka, MN (US); Laurie R. Lawin, New Brighton, MN (US); Byron C. Shen, Eden Prairie, MN (US); Eugene de Juan, La Canada, CA (US); Signe E. Varner, Los Angeles, CA (US); Ralph A. Chappa, Prior Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1408 days.

This patent is subject to a terminal disclaimer.

(21) Appl. No.: 11/225,301

(22) Filed: Sep. 12, 2005

(65) Prior Publication Data
US 2006/0013835 A1 Jan. 19, 2006

Related U.S. Application Data

(63) Continuation of application No. 10/835,530, filed on Apr. 29, 2004.

(60) Provisional application No. 60/467,419, filed on May 2, 2003.

(51) Int. Cl.
*A61F 2/00* (2006.01)

(52) U.S. Cl. ..... 424/428; 424/422; 424/427; 604/890.1; 604/27; 604/36; 606/4

(58) Field of Classification Search ........................... None
See application file for complete search history.

(56) References Cited

U.S. PATENT DOCUMENTS
273,410 A 3/1883 Wadleigh
(Continued)

FOREIGN PATENT DOCUMENTS
EP 0623354 4/1994
(Continued)

OTHER PUBLICATIONS

"Intravitreal Sustained Release Corticosteroid-5-Fluoruracil Conjugate in the Treatment of Experimental Proliferative Vitreoretinopathy," Berger et al, Investigative Ophthalmology & Visual Science, Oct. 1996, vol. 37, No. 2, pp. 2318-2325.

(Continued)

*Primary Examiner* — Anand Desai
*Assistant Examiner* — Melissa Mercier
(74) *Attorney, Agent, or Firm* — Kagan Binder, PLLC

(57) ABSTRACT

The invention provides a controlled release bioactive agent delivery device for treatment of an eye that includes a body member having a direction of extension, a longitudinal axis along the direction of extension, and a proximal end and a distal end, wherein at least a portion of the body member deviates from the direction of extension, and a polymeric coated composition in contact with a surface of the body member, the polymeric coated composition including a first polymer, a second polymer, and a bioactive agent. The first polymer and the second polymer are hydrophobic, and the body member has a length such that, upon placement of the device at an implantation site within a posterior segment of an eye, the device does not enter a central visual field of the eye. The invention also provides methods method of delivering bioactive agent to a posterior region of an eye.

33 Claims, 6 Drawing Sheets

U.S. PATENT DOCUMENTS

| | | | |
|---|---|---|---|
| 3,416,530 A | 12/1968 | Ness | |
| 3,625,214 A | 12/1971 | Higuchi | |
| 4,000,745 A | 1/1977 | Goldberg | |
| 4,069,307 A | 1/1978 | Higuchi et al. | |
| 4,144,317 A | 3/1979 | Higuchi et al. | |
| 4,146,036 A | 3/1979 | Dutcher et al. | |
| 4,206,756 A | 6/1980 | Grossan | |
| 4,209,019 A | 6/1980 | Dutcher et al. | |
| 4,292,965 A | 10/1981 | Nash et al. | |
| 4,300,557 A | 11/1981 | Refojo et al. | |
| 4,304,765 A | 12/1981 | Shell et al. | |
| 4,678,466 A | 7/1987 | Rosenwald | |
| 4,764,377 A | 8/1988 | Goodson | |
| 4,819,661 A | 4/1989 | Heil, Jr. et al. | |
| 4,853,224 A | 8/1989 | Wong | |
| 4,863,457 A | 9/1989 | Lee | |
| 4,892,736 A | 1/1990 | Goodson | |
| 4,953,564 A | 9/1990 | Berthelsen | |
| 4,959,217 A | 9/1990 | Sanders et al. | |
| 4,972,848 A | 11/1990 | Di Domenico et al. | |
| 4,997,652 A | 3/1991 | Wong | |
| 5,002,067 A | 3/1991 | Berthelsen et al. | |
| 5,003,992 A | 4/1991 | Holleman et al. | |
| 5,076,285 A | 12/1991 | Hess et al. | |
| 5,098,443 A | 3/1992 | Parel et al. | |
| 5,114,719 A | 5/1992 | Sabel et al. | |
| 5,164,188 A | 11/1992 | Wong | |
| 5,221,698 A | 6/1993 | Amidon et al. | |
| 5,229,128 A | 7/1993 | Haddad et al. | |
| 5,246,867 A | 9/1993 | Lakowicz et al. | |
| 5,255,693 A | 10/1993 | Dutcher et al. | |
| 5,300,108 A | 4/1994 | Rebell et al. | |
| 5,300,114 A | 4/1994 | Gwon et al. | |
| 5,310,559 A | 5/1994 | Shah et al. | |
| 5,314,419 A | 5/1994 | Pelling | |
| 5,324,325 A | 6/1994 | Moaddeb | |
| 5,364,343 A | 11/1994 | Apolet et al. | |
| 5,372,577 A | 12/1994 | Ungerleider | |
| 5,378,475 A | 1/1995 | Smith et al. | |
| 5,385,148 A | 1/1995 | Lesh et al. | |
| 5,395,618 A | 3/1995 | Darougar et al. | |
| 5,405,376 A | 4/1995 | Mulier et al. | |
| 5,423,777 A | 6/1995 | Tajiri et al. | |
| 5,431,649 A | 7/1995 | Mulier et al. | |
| 5,437,656 A | 8/1995 | Shikani et al. | |
| 5,443,505 A | 8/1995 | Wong et al. | |
| 5,447,724 A | 9/1995 | Helmus et al. | |
| 5,449,382 A | 9/1995 | Dayton | |
| 5,464,650 A | 11/1995 | Berg et al. | |
| 5,466,233 A | 11/1995 | Weiner et al. | |
| 5,472,436 A | 12/1995 | Fremstad | |
| 5,476,511 A | 12/1995 | Gwon et al. | |
| 5,501,856 A | 3/1996 | Ohtori et al. | |
| 5,512,055 A | 4/1996 | Domb et al. | |
| 5,525,348 A | 6/1996 | Whitbourne et al. | |
| 5,545,208 A | 8/1996 | Wolff et al. | |
| 5,554,114 A | 9/1996 | Wallace et al. | |
| 5,556,633 A | 9/1996 | Haddad et al. | |
| 5,578,075 A | 11/1996 | Dayton | |
| 5,582,616 A | 12/1996 | Bolduc et al. | |
| 5,591,227 A | 1/1997 | Dinh et al. | |
| 5,605,696 A | 2/1997 | Eury et al. | |
| 5,609,629 A | 3/1997 | Fearnot et al. | |
| 5,624,411 A | 4/1997 | Tuch | |
| 5,624,975 A | 4/1997 | Valencia | |
| 5,637,113 A | 6/1997 | Tartaglia et al. | |
| 5,645,592 A | 7/1997 | Nicolais et al. | |
| 5,651,986 A | 7/1997 | Brem et al. | |
| 5,679,400 A | 10/1997 | Tuch | |
| 5,725,493 A | 3/1998 | Avery et al. | |
| 5,766,242 A | 6/1998 | Wong et al. | |
| 5,773,019 A | 6/1998 | Ashton et al. | |
| 5,807,395 A | 9/1998 | Mulier et al. | |
| 5,810,836 A | 9/1998 | Hussein et al. | |
| 5,824,072 A | 10/1998 | Wong | |
| 5,830,173 A | 11/1998 | Avery et al. | |
| 5,833,715 A | 11/1998 | Vachon et al. | |
| 5,837,313 A | 11/1998 | Ding et al. | |
| 5,868,697 A | 2/1999 | Richter et al. | |
| 5,877,224 A | 3/1999 | Brocchini et al. | |
| 5,886,026 A | 3/1999 | Hunter et al. | |
| 5,904,144 A | 5/1999 | Hammang et al. | |
| 5,921,982 A | 7/1999 | Lesh et al. | |
| 5,928,662 A | 7/1999 | Philips | |
| 5,972,027 A | 10/1999 | Johnson | |
| 5,972,369 A | 10/1999 | Roorda et al. | |
| 5,980,972 A | 11/1999 | Ding | |
| 5,989,579 A | 11/1999 | Darougar et al. | |
| 5,997,517 A | 12/1999 | Whitbourne | |
| 6,001,386 A | 12/1999 | Ashton et al. | |
| 6,053,924 A | 4/2000 | Hussein | |
| 6,074,661 A | 6/2000 | Olejnik et al. | |
| 6,091,978 A | 7/2000 | Johnson et al. | |
| 6,096,070 A | 8/2000 | Ragheb et al. | |
| 6,099,562 A | 8/2000 | Ding et al. | |
| 6,102,887 A | 8/2000 | Altman | |
| 6,110,483 A | 8/2000 | Whitbourne et al. | |
| 6,117,456 A | 9/2000 | Lee et al. | |
| 6,120,536 A | 9/2000 | Ding et al. | |
| 6,129,933 A | 10/2000 | Oshlack et al. | |
| 6,143,037 A | 11/2000 | Goldstein et al. | |
| 6,153,252 A | 11/2000 | Hossainy et al. | |
| 6,177,095 B1 | 1/2001 | Sawhney et al. | |
| 6,187,370 B1 | 2/2001 | Dinh et al. | |
| 6,197,324 B1 | 3/2001 | Crittenden | |
| 6,203,556 B1 | 3/2001 | Evans et al. | |
| 6,212,434 B1 | 4/2001 | Scheiner et al. | |
| 6,214,008 B1 | 4/2001 | Illi | |
| 6,214,901 B1 * | 4/2001 | Chudzik et al. | 523/113 |
| 6,217,895 B1 | 4/2001 | Guo et al. | |
| 6,248,112 B1 | 6/2001 | Gambale et al. | |
| 6,251,090 B1 | 6/2001 | Avery et al. | |
| 6,251,136 B1 | 6/2001 | Guruwaiya et al. | |
| 6,251,418 B1 | 6/2001 | Ahern et al. | |
| 6,287,285 B1 | 9/2001 | Michal et al. | |
| 6,290,728 B1 | 9/2001 | Phelps et al. | |
| 6,298,272 B1 | 10/2001 | Peterfeso et al. | |
| 6,306,125 B1 | 10/2001 | Parker et al. | |
| 6,306,426 B1 | 10/2001 | Olejnik et al. | |
| 6,309,370 B1 | 10/2001 | Haim et al. | |
| RE37,463 E | 12/2001 | Altman | |
| 6,331,313 B1 | 12/2001 | Wong et al. | |
| 6,344,035 B1 | 2/2002 | Chudzik et al. | |
| 6,358,247 B1 | 3/2002 | Altman et al. | |
| 6,360,129 B1 | 3/2002 | Ley et al. | |
| 6,375,972 B1 | 4/2002 | Guo et al. | |
| 6,399,144 B2 | 6/2002 | Dinh et al. | |
| 6,399,655 B1 | 6/2002 | De Juan et al. | |
| 6,399,704 B1 | 6/2002 | Laurin et al. | |
| 6,451,373 B1 | 9/2002 | Hossainy et al. | |
| 6,478,776 B1 | 11/2002 | Rosenman et al. | |
| 6,497,691 B1 | 12/2002 | Bevins et al. | |
| 6,501,994 B1 | 12/2002 | Janke et al. | |
| 6,505,082 B1 | 1/2003 | Scheiner et al. | |
| 6,506,411 B2 | 1/2003 | Hunter et al. | |
| 6,544,544 B2 | 4/2003 | Hunter et al. | |
| 6,547,787 B1 | 4/2003 | Altman et al. | |
| 6,548,078 B2 | 4/2003 | Guo et al. | |
| 6,562,051 B1 | 5/2003 | Bolduc et al. | |
| 6,585,764 B2 | 7/2003 | Wright et al. | |
| 6,595,958 B1 | 7/2003 | Mickley | |
| 6,613,017 B1 | 9/2003 | Mickley | |
| 6,653,426 B2 | 11/2003 | Alvarado et al. | |
| 6,706,023 B1 | 3/2004 | Huttner et al. | |
| 6,713,081 B2 | 3/2004 | Robinson et al. | |
| 6,716,196 B2 | 4/2004 | Lesh et al. | |
| 6,719,750 B2 * | 4/2004 | Varner et al. | 604/289 |
| 6,719,805 B1 | 4/2004 | Ahern | |
| 6,726,918 B1 | 4/2004 | Wong et al. | |
| 6,764,470 B2 | 7/2004 | Dimick | |
| 2001/0014717 A1 | 8/2001 | Hossainy et al. | |
| 2001/0029351 A1 | 10/2001 | Falotico et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0013298 A1 | 1/2002 | Hunter | |

| | | | |
|---|---|---|---|
| 2002/0018795 A1 | 2/2002 | Whitbourne et al. | |
| 2002/0026176 A1 | 2/2002 | Varner et al. | |
| 2002/0026236 A1 | 2/2002 | Helmus et al. | |
| 2002/0032434 A1 | 3/2002 | Chudzik et al. | |
| 2002/0032477 A1 | 3/2002 | Helmus et al. | |
| 2002/0051730 A1 | 5/2002 | Bodnar et al. | |
| 2002/0054900 A1 | 5/2002 | Kamath et al. | |
| 2002/0091433 A1 | 7/2002 | Ding et al. | |
| 2002/0107330 A1 | 8/2002 | Pinchuk et al. | |
| 2002/0111590 A1 | 8/2002 | Davila et al. | |
| 2002/0114823 A1 | 8/2002 | Sirhan et al. | |
| 2002/0120326 A1 | 8/2002 | Michael | |
| 2002/0133183 A1 | 9/2002 | Lentz et al. | |
| 2002/0138048 A1 | 9/2002 | Tuch | |
| 2002/0165265 A1 | 11/2002 | Hunter et al. | |
| 2002/0168394 A1 | 11/2002 | Hossainy et al. | |
| 2002/0188037 A1 | 12/2002 | Chudzik et al. | |
| 2002/0188170 A1 | 12/2002 | Santamore et al. | |
| 2002/0198511 A1 | 12/2002 | Varner et al. | |
| 2003/0004209 A1 | 1/2003 | Hunter et al. | |
| 2003/0014036 A1 | 1/2003 | Varner et al. | |
| 2003/0021828 A1 | 1/2003 | Guo et al. | |
| 2003/0031780 A1 | 2/2003 | Chudzik et al. | |
| 2003/0054023 A1 | 3/2003 | Hughes | |
| 2003/0060783 A1 | 3/2003 | Koole et al. | |
| 2003/0065332 A1 | 4/2003 | TenHuisen et al. | |
| 2003/0083646 A1 | 5/2003 | Sirhan et al. | |
| 2003/0094736 A1 | 5/2003 | Qin et al. | |
| 2003/0096131 A1 | 5/2003 | Beavers et al. | |
| 2003/0120200 A1 | 6/2003 | Bergheim et al. | |
| 2003/0157187 A1 | 8/2003 | Hunter | |
| 2003/0158598 A1 | 8/2003 | Ashton et al. | |
| 2003/0175324 A1 | 9/2003 | Robinson et al. | |
| 2003/0207856 A1 | 11/2003 | Tremble et al. | |
| 2003/0229333 A1 | 12/2003 | Ashton et al. | |
| 2003/0232087 A1 | 12/2003 | Lawin et al. | |
| 2003/0232122 A1 | 12/2003 | Chappa et al. | |
| 2003/0236513 A1 | 12/2003 | Schwarz et al. | |
| 2003/0236514 A1 | 12/2003 | Schwarz | |
| 2004/0006146 A1 | 1/2004 | Evans et al. | |
| 2004/0022853 A1 | 2/2004 | Ashton et al. | |
| 2004/0034357 A1 | 2/2004 | Beane et al. | |
| 2004/0047911 A1 | 3/2004 | Lyu et al. | |
| 2004/0121014 A1 | 6/2004 | Guo et al. | |
| 2004/0133155 A1 | 7/2004 | Varner et al. | |
| 2004/0137059 A1 | 7/2004 | Nivaggioli et al. | |
| 2004/0142013 A1 | 7/2004 | Rubsamen | |
| 2004/0143314 A1 | 7/2004 | Sommer et al. | |
| 2005/0019371 A1 | 1/2005 | Anderson et al. | |
| 2005/0129732 A1 | 6/2005 | Rubsamen | |
| 2005/0240147 A1 | 10/2005 | Makower et al. | |
| 2005/0271703 A1 | 12/2005 | Anderson et al. | |
| 2005/0271706 A1 | 12/2005 | Anderson et al. | |
| 2005/0276837 A1 | 12/2005 | Anderson et al. | |
| 2005/0281863 A1 | 12/2005 | Anderson et al. | |
| 2005/0287188 A1 | 12/2005 | Anderson et al. | |

FOREIGN PATENT DOCUMENTS

| | | | |
|---|---|---|---|
| EP | 0604022 | | 6/1994 |
| EP | 0734721 | | 3/1996 |
| EP | 0716836 | | 6/1996 |
| EP | 0 414233 | | 10/1996 |
| EP | 0747069 | | 11/1996 |
| EP | 0832655 | | 6/1997 |
| EP | 0 834282 | | 4/1998 |
| EP | 0879595 | | 4/1998 |
| EP | 0923953 | | 6/1998 |
| EP | 0 625887 | | 10/1998 |
| EP | 0945148 | | 9/1999 |
| EP | 1 374924 | | 1/2004 |
| EP | 1 382302 | | 1/2004 |
| EP | 0 754072 | | 1/2005 |
| EP | 1 117351 | | 8/2005 |
| JP | 02-036882 | | 2/1990 |
| JP | 09-194347 | | 7/1997 |
| WO | WO89/05664 | | 6/1989 |
| WO | WO91/12779 | | 9/1991 |
| WO | WO92/15286 | | 9/1991 |
| WO | WO92/11895 | | 7/1992 |
| WO | WO93/15682 | | 8/1993 |
| WO | WO94/21308 | | 9/1994 |
| WO | WO94/21309 | | 9/1994 |
| WO | WO95/03036 | | 2/1995 |
| WO | WO97/10011 | | 3/1997 |
| WO | WO97/37640 | | 10/1997 |
| WO | WO98/17331 | | 4/1998 |
| WO | WO98/32474 | | 7/1998 |
| WO | WO98/58690 | | 12/1998 |
| WO | WO99/01114 | | 1/1999 |
| WO | WO99/36071 | | 7/1999 |
| WO | WO99/38546 | | 8/1999 |
| WO | WO99/55396 | | 11/1999 |
| WO | WO00/02564 | | 1/2000 |
| WO | WO00/12163 | | 3/2000 |
| WO | WO00/21584 | | 4/2000 |
| WO | WO01/08718 | | 2/2001 |
| WO | WO01/23016 | | 4/2001 |
| WO | WO01/30323 | | 5/2001 |
| WO | WO01/32140 | | 5/2001 |
| WO | WO01/36008 | | 5/2001 |
| WO | WO01/78626 | | 10/2001 |
| WO | WO01/87263 | | 11/2001 |
| WO | WO01/87342 | | 11/2001 |
| WO | WO01/87372 | | 11/2001 |
| WO | WO01/87373 | | 11/2001 |
| WO | WO01/87374 | | 11/2001 |
| WO | WO01/87375 | | 11/2001 |
| WO | WO01/87376 | | 11/2001 |
| WO | WO02/26139 | | 4/2002 |
| WO | WO02/26271 | | 4/2002 |
| WO | WO02/26281 | | 4/2002 |
| WO | WO02/017831 | A2 | 7/2002 |
| WO | WO02/056790 | | 7/2002 |
| WO | WO03/022323 | | 3/2003 |
| WO | WO03/026718 | A1 | 4/2003 |
| WO | WO03/063729 | | 8/2003 |
| WO | WO03/064015 | | 8/2003 |
| WO | WO03/065881 | | 8/2003 |
| WO | WO03/099169 | | 12/2003 |
| WO | WO2004/000267 | | 12/2003 |
| WO | WO2004/004821 | | 1/2004 |
| WO | WO2004/028477 | | 4/2004 |

OTHER PUBLICATIONS

"Intravitreal Sustained Release Dexamethasone/5-FU Device in the Treatment of Experimental PVR," Berger et al, Investigative Ophthalmology & Visual Science, Mar. 15, 1994, vol. 35, No. 4, p. 1923.
"Effects of Intravitreal Administration of Steroids on Experimental Subretinal Neovascularization in the Subhuman Primate," Ishibashi, et al, Arch Ophthalmol, May 1985, vol. 103, pp. 708-711.
"Intravitreal Sustained Release Triamcinolone/5-FU Conjugate Suspension in the Treatment of Experimental," Jaffee et al, Investigative Ophthalmology & Visual Science, Mar. 15, 1995, vol. 36, No. 4, p. S161.
"A Multi-Drug Controlled-Release Implant for Intraocular Treatment of Proliferative Vitreoretinopathy," Zhou et al, Proc. Int. Symp. Control. Re. Bioact. Mater., 24 (1997), pp. 625-626.
"Development of a multiple-drug delivery implant for intraocular management of proliferative vitreoretinopathy," Zhou et al, Journal of Controlled Release 55 (1998), pp. 281-295.
"Safety and Pharmacokinetics of an Intraocular Fluocinolone Acetonide Sustained Delivery Device," Jaffe et al, Investigative Ophthalmology & Visual Science, Oct. 2000, vol. 41, No. 11, pp. 3569-3575.
"Development of a Minimally Invasive Intravitreal Implant for Drug Delivery," Varner et al, ARVO Abstracts Online, May 8, 2003 (4 pgs).
"Adjunctive controlled topical application of tetracycline HCI in the treatment of localized persistent or recurrent periodontitis," Flemmig et al, J. Clin. Periodontol 1996; 23:914-921.
"Angiogenesis in a Delayed Revascularization Model Is Accelerated by Angiogenic Oligosaccharides of Hyaluronan," Lees et al, Laboratory Investigation, vol. 73, No. 2, pp. 259-266, 1995.
"Angiogenesis induced by acidic fibroblast growth factor as an alternative method of revascularization for chronic myocardial ischemia," Sellke et al, Surgery 1996, 120:182-188.

"Angiogenic potential of perivascularly delivered aFGF in a porcine model of chronic myocardial ischemia," Lopez et al, American Journal of Physiology 274, H930-H936, 1998.

"Characterization of Glucose-Mediated Insulin Release from Implantable Polymers," Brown et al, Journal of Pharmaceutical Sciences, vol. 85, No. 12, Dec. 1996, pp. 1341-1345.

"c-myc in Vasculoproliferative Disease," Edelman et al, Circulation Research, 1995; 76:176-182.

"Coated stents: local pharmacology," Raman et al, Semin Intervent Cardiol 1998; 3: 133-137.

"How the field of controlled-release technology began, and its central role in the development of angiogenesis research," Folkman, Biomaterials 1990, vol. 11 November.

"In vitro and in vivo studies of subcutaneous hydromorphone implants designed for the treatment of cancer pain," Lesser et al, Pain, 65 (1996) 265-272.

"In Vitro Evaluations of Transdermal Levonorgestrel," Catz et al, Drug Design and Delivery, 1990, vol. 6, pp. 49-60.

"Intravitreal Sustained Release of VEGF Causes Retinal Neovascularization in Rabbits and Breakdown of the Blood-Retinal Barrier in Rabbits and Primates," Ozaki et al, Exp. Eye Res. (1997) 64, 505-517.

"In vivo system to detect long-term continuous release of bioactive interleukin-2 by immunopharmacological depot preparations in nude mice with human tumors," Huland et al, Journal of Cancer Research and Clinical Oncology (1995) 121: 285-290.

"Long-term Protection Against the Effects of Tumor Necrosis Factor by Controlled Delivery of the Soluble p55 TNF Receptor," Eliaz et al, Cytokine, vol. 8, No. 6, (Jun.), 1996: pp. 482-487.

"Mechanisms of drug loading and release kinetics," Whelan et al, Semin Intervent Cardiol 1998; 3: 127-131.

"Clinical Responses Following Periodontal Treatment by Local Drug Delivery," Goodson et al, Journal of Periodontology, Nov. 1985, pp. 81-87.

"Point-Counterpoint: Drug Eluting Stent Euphoria: A Revolutionary Step or Misguided Euphoria?" Jafary, Transcatheter Cardiovascular Therapeutics, 2002.

"A Randomized Comparison of a Sirolimus-Eluting Stent with a Standard Stent for Coronary Revascularization," Morice et al, The New England Journal of Medicine, vol. 346, Jun. 6, 2002, No. 23, pp. 1773-1780.

"Point-Counterpoint: Drug Eluting Stent Euphoria: A Revolutionary Step or Misguided Euphoria?" Jafary, Transcatheter Cardiovascular Therapeutics, 2002, 5 pgs.

"A Randomized Comparison of a Sirolimus-Eluting Stent with a Standard Stent for Coronary Revascularization," Morice et al, The New England Journal of Medicine, vol. 346, Jun. 6, 2002, No. 23, pp. 1773-1780.

"Rapamycin eluting stent: the onset of a new era in interventional cardiology," Serruys et al, Heart 2002; 87; 305-307.

"A Role in Transforming Growth Factor $B_1$ in the Control of Corneal Neovascularization," Friling et al, in vivo 10: 59-64 (1996).

"Stent-Based Delivery of Sirolimus Reduces Neointimal Formation in a Porcine Coronary Model," Suzuki et al, Circulation. 2001; 104:1188-1193.

"Stent development and local drug delivery," Regar et al, British Medical Bulletin 2001; 59: 227-48.

"Twenty-eight-day efficacy and pharmacokinetics of the sirolimus-eluting stent," Klugherz et al, Therapy and Prevention, Coronary Artery Disease 2002, 13:183-188.

Thomas J. Smith, et al, "Intravitreal Sustained-Release Ganciclovir," Ophthalmol.,vol. 110, pp. 255-258 (1992).

George E. Sandorn, et al, "Sustained-Release Ganciclovir Therapy for Treatment of Cytomegalovirus Retinitis," Opthalmol., vol. 110, pp. 188-195 (1992).

* cited by examiner

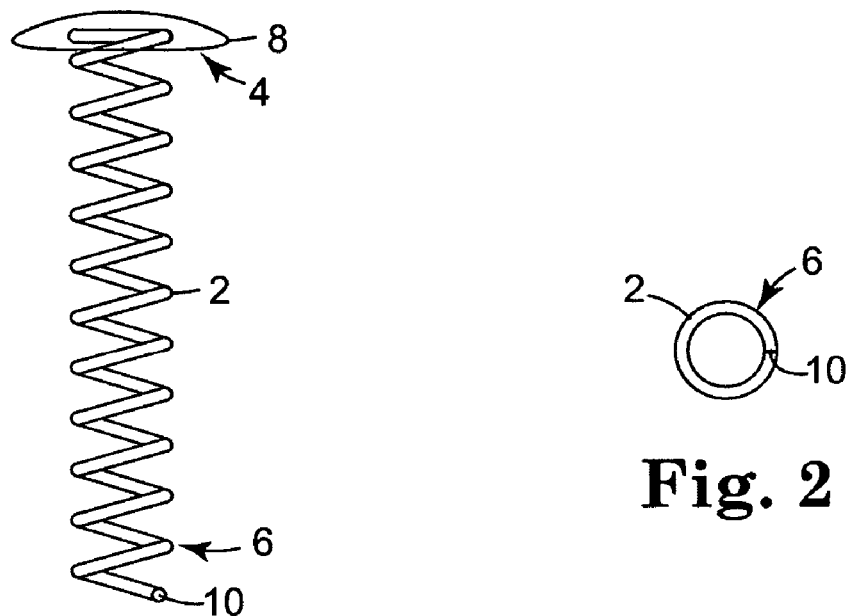
Fig. 1
Fig. 2
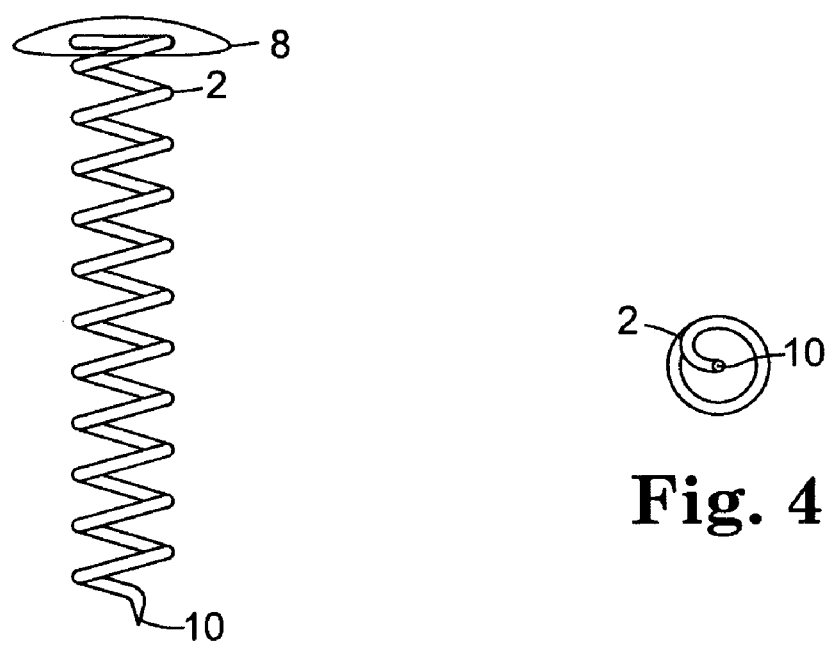
Fig. 3
Fig. 4

CONTROLLED RELEASE BIOACTIVE AGENT DELIVERY DEVICE

This application is a continuation of U.S. application Ser. No. 10/835,530, filed Apr. 29, 2004, entitled "CONTROLLED RELEASE BIOACTIVE AGENT DELIVERY DEVICE," which claims the benefit of U.S. Provisional Application Ser. No. 60/467,419, filed May 2, 2003, entitled "CONTROLLED RELEASE BIOACTIVE AGENT DELIVERY DEVICE," which applications are incorporated herein by reference in their entirety.

FIELD OF THE INVENTION

The invention relates to a delivery device for controlled delivery of one or more bioactive agents to a treatment site within the body.

BACKGROUND OF THE INVENTION

Many surgical interventions involve placement of a medical device into the body. While beneficial for treating a variety of medical conditions, the placement of metal or polymeric devices in the body can give rise to numerous complications. Some of these complications include increased risk of infection, initiation of a foreign body response (which can result in inflammation and/or fibrous encapsulation), and initiation of a wound healing response (which can result in hyperplasia and/or restenosis).

One approach to reducing the potential harmful effects that can result from medical device implantation is to deliver bioactive compounds to the vicinity of the implanted device. This approach attempts to diminish harmful effects that arise from the presence of the implanted device. For example, antibiotics can be released from the surface of the device to minimize infection, and antiproliferative drugs can be released to inhibit hyperplasia. One benefit of the local release of bioactive agents is the avoidance of toxic concentrations of drugs that are sometimes necessary, when given systemically, to achieve therapeutic concentrations at the site where they are required.

Further, medical devices can be placed in the body for treatment of a medical condition, such as infection, disease, or the like. In these instances, one or more bioactive agents can be released from the device to treat the condition, in addition to, or in place of, the bioactive agents that reduce harmful effects of the implant itself.

Several challenges confront the use of medical devices that release bioactive agents into a patient's body. For example, treatment may require release of the bioactive agent(s) over an extended period of time (for example, weeks, months, or even years), and it can be difficult to sustain the desired release rate of the bioactive agent(s) over such long periods of time. Further, the device surface is preferably biocompatible and non-inflammatory, as well as durable, to allow for extended residence within the body. Preferred devices intended for implantation in the body are manufactured in an economically viable and reproducible manner, and they are preferably sterilizable using conventional methods.

In particular, placement of implantable devices in limited access regions of the body can present additional challenges. Limited access regions of the body can be characterized in terms of physical accessibility as well as therapeutic accessibility. Factors that can contribute to physical accessibility difficulties include the size of the region to be reached (for example, small areas such as glands), the location of the region within the body (for example, areas that are embedded within the body, such as the middle or inner ear), the tissues surrounding the region (for example, areas such as the eye or areas of the body surrounded by highly vascularized tissue), or the tissue to be treated (for example, when the area to be treated is composed of particularly sensitive tissue, such as areas of the brain).

Factors that can contribute to therapeutic accessibility can be seen, for example, in the delivery of drugs to the eye. Ocular absorption of systemically administered pharmacologic agents is limited by the blood ocular barrier, namely the tight junctions of the retinal pigment epithelium and vascular endothelial cells. High systemic doses of bioactive agents can penetrate this blood ocular barrier in relatively small amounts, but expose the patient to the risk of systemic toxicity. Intravitreal injection of bioactive agents (such as drugs) is an effective means of delivering a drug to the posterior segment of the eye in high concentrations. However, these repeated injections carry the risk of such complications as infection, hemorrhage, and retinal detachment. Patients also often find this procedure somewhat difficult to endure.

Because description of the invention will involve treatment of the eye as an illustrative embodiment, basic anatomy of the eye will now be described in some detail with reference to FIG. 5, which illustrates a cross-sectional view of the eye. Beginning from the exterior of the eye, the structure of the eye includes the iris 38 that surrounds the pupil 40. The iris 38 is a circular muscle that controls the size of the pupil 40 to control the amount of light allowed to enter the eye. A transparent external surface, the cornea 30, covers both the pupil 40 and the iris 38. Continuous with the cornea 30, and forming part of the supporting wall of the eyeball, is the sclera 28 (the white of the eye). The conjunctiva 32 is a clear mucous membrane covering the sclera 28. Within the eye is the lens 20, which is a transparent body located behind the iris 38. The lens 20 is suspended by ligaments attached to the anterior portion of the ciliary body (not illustrated in the figures). The contraction or relaxation of these ligaments as a consequence of ciliary muscle actions changes the shape of the lens 20, a process called accommodation, and allows a sharp image to be formed on the retina 24. Light rays are focused through the transparent cornea 30 and lens 20 upon the retina 24. The central point for image focus (the visual axis) in the human retina is the fovea (not shown in the figures). The optic nerve 42 is located opposite the lens.

There are three different layers of the eye, the external layer, formed by the sclera 28 and cornea 30; the intermediate layer, which is divided into two parts, namely the anterior (iris 38 and ciliary body) and posterior (the choroid 26); and the internal layer, or the sensory part of the eye, formed by the retina 24. The lens 20 divides the eye into the anterior segment (in front of the lens) and the posterior segment (behind the lens). More specifically, the eye is composed of three chambers of fluid: the anterior chamber 34 (between the cornea 30 and the iris 38), the posterior chamber 36 (between the iris 38 and the lens 20), and the vitreous chamber 22 (between the lens 20 and the retina 24). The anterior chamber 34 and posterior chamber 36 are filled with aqueous humor whereas the vitreous chamber 22 is filled with a more viscous fluid, the vitreous humor.

An implantable medical device that can undergo flexion and/or expansion upon implantation, and that is also capable of delivering a therapeutically significant amount of a pharmaceutical agent or agents from the surface of the device has been described. See U.S. Pat. Nos. 6,214,901 and 6,344,035, published PCT Application No. WO99/55396 and U.S. Patent Application Publication Nos. 2002/0032434, 2003/0031780, and 2002/0188037.

A therapeutic agent delivery device that is particularly suitable for delivery of a therapeutic agent to limited access regions, such as the vitreous chamber of the eye and inner ear is described in U.S. Patent Application Publication No. 2002/0026176 A1.

SUMMARY OF THE INVENTION

The present invention provides devices and methods for providing one or more bioactive agents to a treatment site within the body in a controllable manner. The invention can provide particular advantages when used to deliver bioactive agent(s) to limited access regions of the body. Preferred embodiments of the invention relate to devices and methods for providing bioactive agent(s) to treatment sites in a manner that minimizes damage and interference with body tissues and processes. A primary function of the inventive device is to deliver the bioactive agent(s) to a desired treatment site within the body, and in preferred embodiments, the device itself does not provide any other significant function. That is, once the desired treatment of the body has been accomplished, the device is preferably removed from the body. Moreover, preferred embodiments of the invention provide a device that is minimally invasive such that risks and disadvantages associated with more invasive surgical techniques can be reduced.

In one aspect, the invention relates to a controlled release bioactive agent delivery device comprising (a) a body member having a direction of extension, a longitudinal axis along the direction of extension, and a proximal end and a distal end, wherein at least a portion of the body member deviates from the direction of extension; and (b) a coating composition in contact with the body member, the coating composition comprising a bioactive agent. Preferably, the coating composition is a polymeric coating composition.

In another aspect, the invention relates to a controlled release bioactive agent delivery device comprising (a) a body member having a direction of extension, a longitudinal axis along the direction of extension, and a proximal end and a distal end, wherein at least a portion of the body member deviates from the direction of extension; and (b) a polymeric coated composition in contact with the body member, the polymeric coated composition comprising a first polymer, a second polymer, and a bioactive agent, wherein the first polymer comprises polyalkyl(meth)acrylate, aromatic poly(meth)acrylate, or a combination of polyalkyl(meth)acrylate and aromatic poly(meth)acrylate, and wherein the second polymer comprises poly(ethylene-co-vinyl acetate).

In another aspect, the invention provides methods for delivering one or more bioactive agents to an implantation site within a patient in a controllable manner. In preferred embodiments, the invention provides devices and methods for providing controlled release of one or more bioactive agents to limited access regions of the body, such as the eye, ear, central nervous system, and the like.

In yet another aspect, the invention provides methods of making a controlled release bioactive agent delivery device comprising (a) providing a body member having a direction of extension, a longitudinal axis along the direction of extension, and a proximal end and a distal end, wherein at least a portion of the body member deviates from the direction of extension; and (b) providing a polymeric coating composition comprising a first polymer, a second polymer, and a bioactive agent in contact with the body member, wherein the first polymer comprises polyalkyl(meth)acrylate, aromatic poly(meth)acrylate, or a combination of polyalkyl(meth)acrylate and aromatic poly(meth)acrylate, and wherein the second polymer comprises poly(ethylene-co-vinyl acetate).

For ease of discussion, reference will repeatedly be made to a "bioactive agent." While reference will be made to a "bioactive agent," it will be understood that the invention can provide any number of bioactive agents to a treatment site. Thus, reference to the singular form of "bioactive agent" is intended to encompass the plural form as well.

Preferred embodiments of the invention provide the ability to control release of a bioactive agent by manipulation of one or more features of the controlled release device, including formulation of the coating composition, duration of time the device is maintained at the implantation site, and configuration of the device. For example, the formulation of the coating composition can be manipulated to provide controlled release of the bioactive agent. According to the invention, the coating composition can include any number of individual bioactive agents. Moreover, the coating composition can include a wide variety of types of bioactive agents, as the formulation of the coating composition (for example, the choice and/or ratio of first polymer and second polymer) can be manipulated to accommodate a bioactive agent of choice. Further, the amount of bioactive agent included in the coating composition can be manipulated to provide a desired initial concentration of bioactive agent within the coating composition, thereby providing a selected therapeutic amount of the bioactive agent to the treatment site.

The duration of time the device is maintained at the implantation site can be varied to provide a desired amount of bioactive agent to a treatment site. For example, preferred embodiments of the inventive device are configured to be implanted and explanted from a patient; thus, the device can be removed from the patient at any time an interventionalist determines a treatment course has been completed.

In some embodiments, the configuration of the device can be manipulated to control release of the bioactive agent. For example, the surface area and/or size of the device can be manipulated to control dosage of the bioactive agent(s) provided to the implantation site. In preferred embodiments, the geometry and/or surface area of the body member can be manipulated by choice of wire diameter, coil spacing, device length, device diameter, and the like. Preferably, the device provides increased surface area for delivery of bioactive agent, as compared to a substantially linear device having the same length and width. This increased surface area can be desirable when the implantation site will better accommodate a shorter device (for example, in the eye), or a more narrow device.

Preferably, the configuration of the controlled release device provides one or more mechanical advantages, such as a built-in anchoring mechanism that reduces or prevents unwanted movement of the device within the body, reduced risk of unwanted ejection of the device from the body, and the like. Moreover, preferred embodiments of the invention can provide minimally invasive devices and methods for delivering one or more bioactive agents to a treatment site within the body. Accordingly, the invention can, in some embodiments, reduce risks of infection and complications associated with more invasive surgical procedures, as well as improve recovery time for patients requiring such treatments.

In preferred embodiments, the inventive device is easily retrievable from the body, such that the device is placed within the body only for the required treatment duration, and is removed upon completion of a treatment course. Preferably, the device provides enhanced durability of the coated composition, and thus the coated composition (minus the released bioactive agent) is removed from the implantation site upon completion of a treatment course. This can avoid potential harmful effects that could arise if one or more components of the device were left within the body beyond the treatment course (for example, if some of the coating is sheared off the device or otherwise delaminates from the body member).

Surprisingly, preferred embodiments of the invention provide devices and methods of reproducibly releasing bioactive agent in a linear manner over extended periods of time. As described herein, in vitro elution assays of preferred embodiments of the invention show surprisingly controllable release of bioactive agent over time. In preferred embodiments, coating compositions having varying formulations (in terms of polymer ratios) can provide substantially linear release rates of bioactive agent. Based upon the in vitro data presented herein, it is expected that in vivo release rates will provide reproducible release rates in a linear manner over an extended period of time. See Jaffe et al., *Safety and Pharmacokinetics of an Intraocular Fluocinolone Acetonide Sustained Delivery Device*, Investigative Ophthalmology & Visual Science, 41:3569-3575 (2000). Thus the invention can provide controlled release of bioactive agent to an implantation site that can be adjusted to accommodate desired treatment duration and dosage. Because the invention provides local delivery of one or more bioactive agents to an implantation site, the invention also preferably avoids toxic levels of bioactive agents that can be required during systemic treatment.

Preferably, the invention provides a surprisingly durable controlled release device. Durability can be imparted by material characteristics of the device, as well as structural features of the inventive device. Regarding material characteristics of the device, for example, durability of the device can be described in terms of the chemical composition of the polymeric coating composition, as well as adherence of the polymeric coating composition to the body member. In preferred embodiments, the polymeric coating preferably adheres to the body member sufficiently to withstand the effect of shear forces encountered during implant and/or explant of the device, which could otherwise result in delamination of the coating from the body member. Such adherence can arise from the chemical composition of the polymeric coating, as well as the cohesion of the polymeric coating (thus impacting the integrity of the coating).

Structural features can also provide preferred durability characteristics to the inventive device. According to the invention, at least a portion of the body member deviates from the direction of extension, thereby providing a device that provides structural durability before, during, and after implantation in the body. The structure of the body member is preferably chosen to effectively translate force applied by an interventionalist during implantation and/or explantation to provide desired advanceability (described herein) and thus withstand forces that can compromise the structural integrity of the device. Moreover, when the surface of the body member includes surface configurations (for example, microetched surfaces, roughened surfaces, and the like), adhesion of the polymeric coating composition to the body member surface can be improved.

Durability of the coating composition can be assessed utilizing such techniques as visual inspection of the integrity of the coating on the surface of the body member (for example, utilizing such common techniques as microscopic or spectroscopic analysis), weight of the coating before and after implant/explant, and the like.

These and other aspects and advantages will now be described in more detail.

BRIEF DESCRIPTION OF THE DRAWINGS

The accompanying drawings, which are incorporated in and constitute a part of this specification, illustrate several aspects of the invention and together with the description of the preferred embodiments, serve to explain the principles of the invention. A brief description of the drawings is as follows:

FIG. 1 is a perspective view of an implantable device according to one embodiment of the invention.

FIG. 2 is a view from the bottom of the embodiment illustrated in FIG. 1.

FIG. 3 is a perspective view of an implantable device according to another embodiment of the invention.

FIG. 4 is a view from the bottom of the embodiment illustrated in FIG. 3.

DETAILED DESCRIPTION OF THE INVENTION

Figure 5:
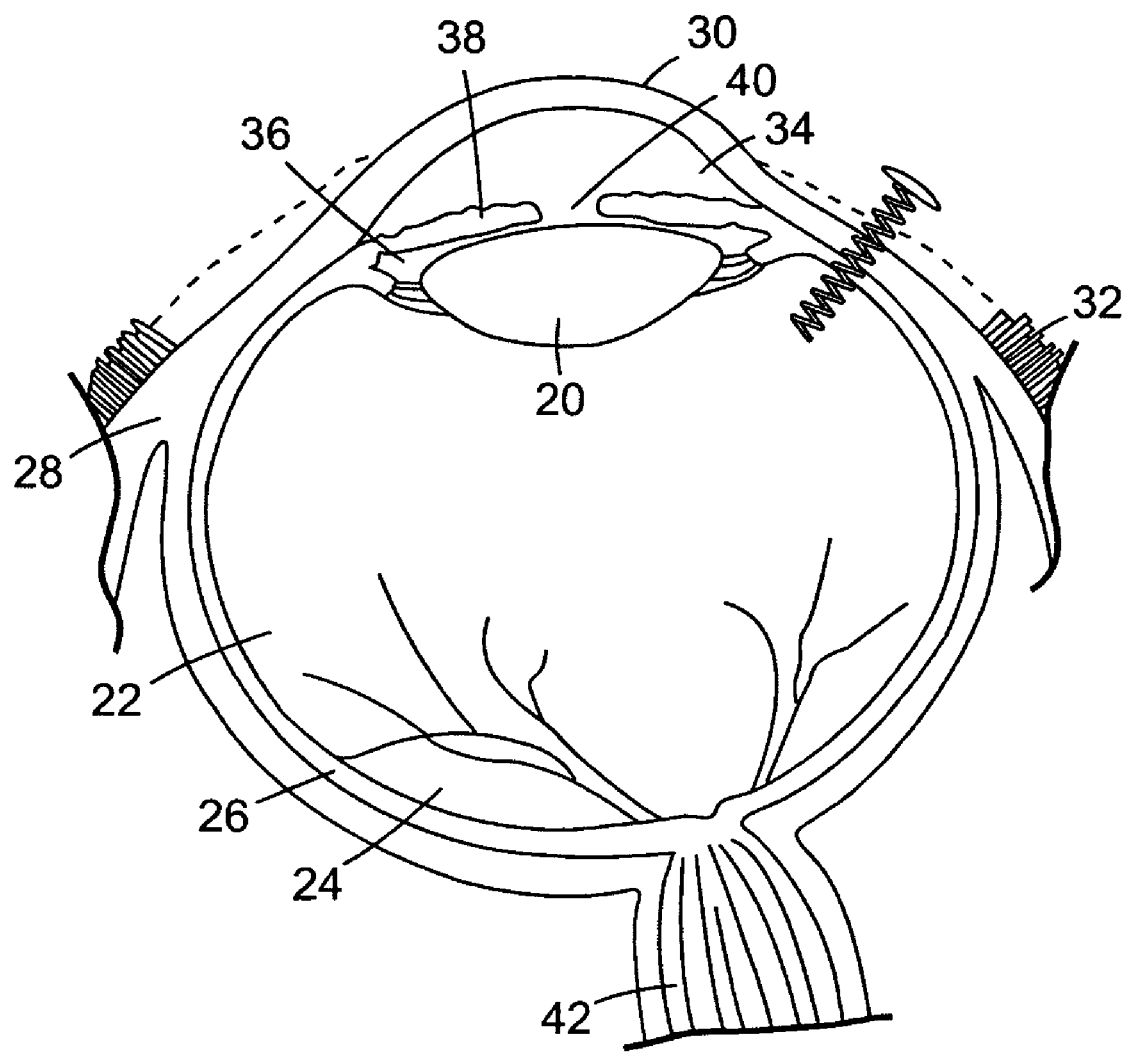
FIG. 5 illustrates transcleral placement of an implantable device according to one embodiment of the invention.

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

Various terms relating to the systems and methods of the invention are used throughout the specification.

As used herein, a "coating composition" refers to one or more vehicles (for example, solutions, mixtures, emulsions, dispersions, blends, and the like) used to effectively coat a surface. A "coated composition" refers to the effective combination of bioactive agent, first polymer, and second polymer on a surface of the controlled delivery device. The coated composition can be formed from one or more coating compositions, or in one or more layers, as will be apparent from the teaching herein.

As used herein, "biocompatible" means the ability of an object to be accepted by and to function in a recipient without eliciting a significant foreign body response (such as, for example, an immune, inflammatory, thrombogenic, or the like response). For example, when used with reference to one or more of the polymers of the invention, biocompatible refers to the ability of the polymer (or polymers) to be accepted by and to function in its intended manner in a recipient.

As used herein, "therapeutically effective amount" refers to that amount of a bioactive agent alone, or together with other substances (as described herein), that produces the desired effect (such as treatment of a medical condition such as a disease or the like, or alleviation of pain) in a patient. During treatment, such amounts will depend upon such factors as the particular condition being treated, the severity of the condition, the individual patient parameters including age, physical condition, size and weight, the duration of the treatment, the nature of the particular bioactive agent thereof employed and the concurrent therapy (if any), and like factors within the knowledge and expertise of the health practitioner. A physician or veterinarian of ordinary skill can readily determine and prescribe the effective amount of the bioactive agent required to treat and/or prevent the progress of the condition.

The term "implantation site" refers to the site within a patient's body at which the implantable device is placed according to the invention. In turn, a "treatment site" includes the implantation site as well as the area of the body that is to receive treatment directly or indirectly from a device component. For example, bioactive agent can migrate from the implantation site to areas surrounding the device itself, thereby treating a larger area than simply the implantation site. The term "incision site" refers to the area of the patient's body (the skin and transdermal area) at which an incision or surgical cut is made to implant the device according to the invention. The incision site includes the surgical cut, as well as the area in the vicinity of the surgical cut, of the patient.

The term "treatment course" refers to the dosage rate over time of one or more bioactive agents, to provide a therapeutically effective amount to a patient. Thus, factors of a treatment course include dosage rate and time course of treatment (total time during which the bioactive agent(s) is administered).

The present invention is directed to methods and apparatuses for effectively treating a treatment site within a patient's body, and in particular for delivering bioactive agents to a limited access region of a patient's body, such as the eye, ear, spinal cord, brain, and joints. Such methods and apparatuses in accordance with the present invention can advantageously be used to provide flexibility in treatment duration and type of bioactive agent delivered to the treatment site. In particular, the present invention has been developed for controllably providing one or more bioactive agents to a treatment site within the body for a desired treatment course.

In order to be properly introduced and utilized, implantable devices of all sorts of types are preferably designed to accommodate needs for advanceability, manipulability, and crossability to the distal end of the device as such is applied to the proximal end of the device. For purposes of this application, the following terms are given the following meaning. Advanceability is the ability to transmit force from the proximal end of the device to the distal end of the device. The body member of the device should have adequate strength for advanceability and resistance to buckling or kinking. Manipulability is the ability to navigate tortuous vasculature or other body passages to reach the treatment site. A more flexible distal portion is known to improve manipulability. Thus, it can be desirable to provide a device having a body member with some elastomeric properties to improve flexibility in some applications. Crossability is the ability to navigate the device across tissue barriers or narrow restrictions in the vasculature.

Optimization of advanceability, manipulability, crossability and torque transmission can be accomplished by carefully choosing the device material and its physical characteristics, such as thickness of the material forming the body member. Further, in order to achieve a combination of desired properties at different parts of the device itself, the device can be fabricated to combine a plurality of components together to define a device body member. That is, a portion of the overall length of a body member of the device can comprise a different component than another. These one or more portions can comprise components of different physical characteristics and/or different materials. For example, a distal tip portion can be provided that is more resilient than the remainder of the device body member for better crossability and to provide a softer leading end of the device for abutting body internal membranes and the like. Different materials include different metallic materials or polymeric materials from one another, for example, or similar polymers of different densities, fillers, crosslinking or other characteristics. In particular, a portion of a device body member can comprise a material chosen for flexibility to allow flexion of the device during residence within the body (for example, in such areas as joints, where movement of the tissues in the area is likely) while another portion can comprise a material chosen for axial and/or torque transmission.

According to the present invention, a device has been developed that can be used to treat any implantation site within the body in which it is desirable to provide controlled release of one or more bioactive agents. In preferred embodiments, the device can be used to provide one or more bioactive agents to a treatment site that comprises a limited access region of the body, such as the eye, ear, brain, spine, and joints. More specifically, the device of the invention includes a body member having a direction of extension and at least a portion of the body member deviating from the direction of extension, and a polymeric coating composition in contact with the body member. The body member and polymeric coating composition are configured to provide controlled release of a bioactive agent to a treatment site. As described herein, controlled release at the treatment site can mean control both in dosage (including dosage rate and total dosage) and duration of treatment.

To facilitate the discussion of the invention, use of the invention to treat an eye will be addressed. Eyes are selected as a result of the particular difficulties encountered when treating medical conditions of the eye, as described above. Further, in terms of lowering the risk of damage to body tissues while providing a superior device, the advantages of this controlled release device can be clearly presented. However, it is understood that the device and methods disclosed are applicable to any treatment needs, for example, treatment of limited access regions of the body where controlled release of a bioactive agent is desired during treatment, such as, for example, the central nervous system (the brain and spinal cord), the ear (such as the inner ear), and joints.

In one aspect, the invention provides a controlled release bioactive agent delivery device comprising: (a) a body member having a direction of extension, a longitudinal axis along the direction of extension, and a proximal end and a distal end, wherein at least a portion of the body member deviates from the direction of extension; and (b) a polymeric coated composition in contact with the body member, the polymeric coated composition comprising a first polymer, a second polymer, and a bioactive agent, wherein the first polymer comprises polyalkyl(meth)acrylate, aromatic poly(meth)acrylate, or a combination of polyalkyl(meth)acrylate and aromatic poly(meth)acrylate, and wherein the second polymer comprises poly(ethylene-co-vinyl acetate).

Generally speaking, the body member of the implantable device is the portion of the controlled release device that is inserted into a patient. The body member can be described as including a proximal end (which is located, upon implantation, towards the exterior of the body), a distal end (which is located, upon implantation, towards the interior of the body), and a longitudinal axis. In use, at least a portion of the body member is inserted into a patient's body. For example, in some embodiments, it can be preferable to position less than 100% of the body member inside the patient's body. The amount of the body member positioned within the body can be determined by the interventionalist, based upon such factors as desired treatment parameters, the particular configuration of the device, the implantation site, and the like.

The body member further includes a direction of extension, and in preferred embodiments, at least a portion of the body member deviates from the direction of extension. In preferred embodiments, the body member includes at least two, three, four, five, six, seven, eight, nine, ten, or more deviations from the direction of extension. In some alternative embodiments, where the body does not include multiple deviations from the direction of extension, the body member can be provided in a "J" or a hook-type configuration.

The deviations from the direction of extension can be provided in any suitable configuration. Exemplary embodiments of such deviations will be described herein for illustrative purposes only, and without intending to be bound by any particular embodiment described herein. The deviations need not be rounded or arcuate. For example, in some embodiments, the body member is provided with a Z-shaped configuration, such that the deviations are angular. Moreover, the deviations need not be in a regular pattern, but can alternatively be provided in a random manner, such that the body member contains random curls or turns. In some embodiments, the deviations are provided in a patterned configuration about the longitudinal axis. Examples of these patterned embodiments include coils, spirals, or patterned Z-shaped turns in the body. Alternatively, the deviations can be provided in a random or non-patterned configuration about the longitudinal axis. According to these particular non-patterned embodiments, the distance of the individual deviations from the longitudinal axis to the outermost periphery of the body member can be selected to provide a desired overall profile of the body member, depending upon the application of the device. For example, it can be desirable, in some applications, to provide an overall profile of the body member having an hourglass shape, alternating ring circumference shapes, and the like.

In some embodiments, the deviations from the direction of extension can be provided in the form of rings. Such individual rings can be concentric (that is, having a common axis, or being coaxial about the longitudinal axis) or eccentric (deviating from a circular path). According to these embodiments, the individual rings are noncontiguous along the body member length, thereby forming individual ribs at positions along the direction of extension of the body member.

Preferred configurations of the body member are coiled or spiral. Generally, in a coil configuration, the individual rings of the coil rotate about the longitudinal axis, and the overall coil is substantially symmetrical about the longitudinal axis. A preferred coil is composed of multiple rings that are substantially similar in circumference along the length, from proximal to distal, of the device. In some preferred embodiments, the rings form a spiral pattern, wherein the circumference of the rings changes over the length of the device. Preferably, the circumference of the rings decreases toward the distal direction of the device, so that the largest ring circumference is located at the proximal region of the device, and the smallest ring circumference is located at the distal region of the device.

Inclusion of deviating portions of the body member provides an increased surface area for delivery of a bioactive agent to an implantation site as compared to a linear device having the same length and/or width. This can provide advantages during use of the device, since this configuration allows a greater surface area to be provided in a smaller length and/or width of the device. For example, in some applications, it can be desirable to limit the length of the device. For example, as will be discussed in more detail herein, it is desirable to limit the length of implants in the eye to prevent the device from entering the central visual field of the eye and to minimize risk of damage to the eye tissues. By providing a body member that has at least a portion of the body member deviating from the direction of extension, the device of the invention has greater surface area (and thus can hold a greater volume of bioactive agent) per length of the device without having to make the cross section of the device, and thus the size of the insertion incision, larger.

Still further, in preferred embodiments, the shape of the body member can provide a built-in anchoring system that reduces unwanted movement of the device and unwanted ejection of the device out of the patient's body, since the shape of the body member requires manipulation to remove it from an incision. For example, for a coil-shaped body member, the device would require twisting, and a Z-shaped body member would require back and forth movement, to remove the device from the implantation site. According to some preferred embodiments, the device does not require additional anchoring mechanisms (such as suturing) to the body tissues, as a result of the self-anchoring characteristics of the device itself. As described in more detail herein, inclusion of a cap 8 on the device can provide further anchoring features of the device.

In some embodiments, when the body member includes two or more deviations from the direction of extension, the spacing of the individual deviations can be selected to provide an optimum combination of such features as increased coatable surface area, overall dimensions of the device, and the like. For example, when the body member is provided in the form of a coil that includes two or more deviations from the direction of extension, the distance between the individual coils can be selected to be equal to or greater than the diameter of the material forming the body member. In some aspects, if the distance between coils is less than the diameter of the material forming the body member, the amount of coatable surface area of the body member can decrease, since it can be more difficult to access portions of the surface area of the body member with the coating compositions. In one illustrative embodiment of this aspect of the invention, the body member is formed of a material having a diameter of 0.5 mm, and the distance between each coil of the body member is at least 0.5 mm. These principals can be applied to any configuration of the body member and is not limited to coiled configurations.

The overall dimensions of the implantable device can be selected according to the particular application. For example, the length and/or width of the device can be selected to accommodate the particular implantation site. Some factors that can affect the overall dimensions of the implantable device include the potency of any bioactive agent to be delivered (and thus the volume of bioactive agent required, which impacts the surface area of the device, as discussed herein), the location of the implantation site within the body (for example, how far within the body the implantation site is located), the size of the implantation site (for example, a small area such as the eye or inner ear, or a larger area, such as a joint or organ area), the tissue surrounding the implantation site (for example, vascular tissue or hard, calcinous tissue, such as bone), and the like.

By way of example, when the implantable device is used to deliver bioactive agent(s) to the eye, the device is preferably designed for insertion through a small incision that requires few or no sutures for scleral closure at the conclusion of the surgical procedure. As such, the device is preferably inserted through an incision that is no more than about 1 mm in cross-section, for example, in the range of about 0.25 mm to about 1 mm in diameter, preferably in the range of about 0.25 mm to about 0.5 mm in diameter. As such, the cross-section of the material forming the body member 2 is preferably no more than about 1 mm, for example, in the range of about 0.25 mm to about 1 mm in diameter, preferably in the range of about 0.25 mm to about 0.5 mm in diameter. When the material forming the body member 2 is not cylindrical, the largest dimension of the cross-section can be used to approximate the diameter of the body member for this purpose, for example, when the body member cross-section is square.

When used to deliver bioactive agent(s) to the eye, the body member of the controlled release device preferably has a total length from its proximal end to its distal end that is less than about 1 cm, for example, in the range of about 0.25 cm to about 1 cm. Upon implantation, the body member is positioned within the eye, such that the portion of the controlled delivery device that delivers bioactive agent to the eye chamber is positioned near the posterior segment of the eye. When the controlled delivery device includes a cap 8, the cap is preferably provided with a thickness of less than about 1 mm, more preferably less than about 0.5 mm. According to this particular embodiment, the total length of the controlled delivery device is less than about 1.1 cm, preferably less than about 0.6 cm.

Turning to FIG. 1, a preferred embodiment of the controlled delivery device is illustrated. The controlled delivery device includes a body member 2 having a proximal end 4 and a distal end 6. FIG. 1 illustrates the body member in a coil configuration. According to this embodiment, the coil shape of the body member allows the device to be screwed or twisted into the body through an incision approximately the same size as the outer diameter of the material forming the body member 2. Still further, the coil shape of the body member can act as an anchoring mechanism to maintain the controlled delivery device within the implantation site, and can prevent unwanted movement of the device and unwanted ejection of the device from the implantation site and/or the body. As a result of the coil shape, the controlled delivery device is twisted and unscrewed out of the body during removal of the device.

The distal end 6 of the body member 2 can be positioned at any desirable location relative to the longitudinal axis of the body member. As shown in FIGS. 1 and 2, the distal end 6 of the body member according to one embodiment of the invention can include a tip 10 that is spaced from the longitudinal axis. This configuration is similar to a standard "cork screw" type configuration. In use, the device is inserted through the incision site and then twisted until the controlled delivery device is properly positioned at the treatment site.

Another embodiment is shown in FIGS. 3 and 4, wherein the distal end 6 of the body member includes tip 10 that is positioned at the longitudinal axis of the body member 2. In some embodiments, placement of the tip 10 of the body member 2 at the longitudinal axis can provide advantages, such as ease of insertion of the device at the distal end. It will be readily apparent that various other configurations of the distal end of the body member can be provided, depending upon the desired application.

Further, the proximal end 4 of the body member 2 can also be positioned at any desirable location relative to the longitudinal axis of the body member. FIGS. 1 and 3 illustrate the proximal end 4 of the body member as spaced from the longitudinal axis. However, the proximal end 4 of the body member can be provided at the longitudinal axis as well (not shown in the figures). In some embodiments, placement of the proximal end 4 of the body member 2 at the longitudinal axis can provide advantages, such as ease of fabrication of the device, increased mechanical strength, improved translation of force (since a uniform force can be applied and translated to the body member, with less risk of bending or other deformation of the body member), and the like.

In general, materials used to fabricate the body member 2 are not particularly limited. In some embodiments, the body member 2 can be fabricated of a flexible material, so that small movements of the controlled delivery device will not be translated to the implantation site. In some embodiments, as described in further detail herein, it can be preferable to fabricate at least the distal end 6 of the body member 2 of a rigid, non-pliable material. For example, when the device is designed for implantation in the eye, it is preferable to fabricate the device of a rigid material, to provide improved implant/explant characteristics to the device. In some embodiments, as described herein, it can be preferable to fabricate the body member 2 of a material having shape memory and/or superelastic characteristics.

In some embodiments, the body member 2 can be fabricated from any suitable material used to manufacture medical devices, such as, for example, stainless steel (for example, 316L); platinum; titanium; and gold; and such alloys as cobalt chromium alloys, nitinol, or the like. In further embodiments, suitable ceramics can be used to fabricate the body member 2, such as, for example, silicon nitride, silicon carbide, zirconia, alumina, glass, silica, sapphire, and the like. In still further embodiments, the body member 2 can be fabricated of a suitable composite material, such as composite materials commonly used to fabricate implantable devices. Such composite materials can, in some embodiments, provide such advantages as increased strength of the material, as well as increased flexibility. Examples of suitable composite materials include polymers or ceramics (such as high density polyethylene (HDPE), ultra high molecular weight polyethylene (UHMWPE), polymethylmethacrylate bone cement (PMMA), dental polymer matrix (such as crosslinked methacrylate polymers), and glass-ceramics) reinforced with fibers or particulate material (such as carbon fibers, bone particles, silica particles, hydroxyapatite particles, metal fibers or particles, or zirconia, alumina, or silicon carbide particles). Nano-composite materials are also contemplated.

In one embodiment, the body member 2 is fabricated of a nonbiodegradable polymer. Such nonbiodegradable polymers are well known and can include, for example, oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; and vinyls such as ethylene, propylene, styrene, vinyl chloride, vinyl acetate, and vinylidene difluoride. Examples of condensation polymers include, but are not limited to, nylons such as polycaprolactam, polylauryl lactam, polyhexamethylene adipamide, and polyhexamethylene dodecanediamide, as well as polyurethanes, polycarbonates, polyamides, polysulfones, poly(ethylene terephthalate), polylactic acid, polyglycolic acid, polydimethylsiloxanes, and polyetherketone. Other suitable nonbiodegradable polymers include silicone elastomers; silicone rubber; polyolefins such as polypropylene and polyethylene; homopolymers and copolymers of vinyl acetate such as ethylene vinyl acetate 2-pyrrolidone copolymer; polyacrylonitrile butadiene; fluoropolymers such as polytetrafluoroethylene and polyvinyl fluoride; homopolymers and copolymers of styrene acrylonitrile; homopolymers and copolymers of acrylonitrile butadiene styrene; polymethylpentene; polyimides; natural rubber; polyisobutylene; polymethylstyrene; latex; and other similar nonbiodegradable polymers.

At least a portion of the body member 2 can deviate from the direction of extension prior to, during, and after insertion of the device in the body. Alternatively, the device can be fabricated of a material having shape memory and/or superelastic characteristics that allow the device to be deformed into a configuration that is more easily inserted into the body. In one such embodiment, for example, the body member can be deformed into a substantially linear configuration, for insertion into the body. According to this particular embodiment, the body member can return to its original shape after it is inserted into the body. In this embodiment, the body member of the device has a "memory shape" that it will assume under certain conditions. For example, the body member can have a zigzag or coiled memory shape. When the interventionalist desires to implant the device into the body, the interventionalist can deform the device into a substantially linear shape for insertion of the device through an incision the size of the cross section of the linear shaped device. Upon implantation of the device into the body, the device can then resume its zigzag, coiled, or other memory shape. Preferably, the overall dimensions of the controlled delivery device (the maximum length and width) according to these shape memory embodiments do not significantly change by virtue of utilization of the shape memory material and deformation of the body member for implantation and/or explantation of the device in the body.

Shape memory alloys generally have at least two phases, namely, a martensite phase, which has a relatively low tensile strength and which is stable at relatively low temperatures, and an austenite phase, which has a relatively high tensile strength and which is stable at temperatures higher than the martensite phase. The shape memory characteristics are imparted to the material by heating the material to a temperature above the temperature at which the austenite phase is stable. While the material is heated to this temperature, the device is held in the "memory shape," which is the shape that is desired to be "remembered." Materials having shape memory and/or superelastic characteristics are well known and can include, for example, shape memory alloys (SMA) such as nitinol (a nickel-titanium alloy), and shape memory polymers (SMP) such as AB-polymer networks based upon oligo(e-caprolactone) dimethylacrylates and n-butyl acrylate. Such materials and methods of imparting shape memory characteristics are known and will not be described further herein.

Preferably, the controlled delivery device of the invention takes advantage of the material properties of the body member (for example, superelastic properties) to extend the body member into a linear shape. Once placed at the implantation site in an unconstrained form, the body member can resume its memory shape.

The distal end 6 of the body member can include any suitable configuration, depending upon the application of the device and the site of the body at which the device is to be implanted. For example, in some embodiments, the distal end 6 can be blunt or rounded. In preferred embodiments, the distal end 6 of the body member is configured to pierce the body during implantation of the device into the body. For example, the distal end 6 of the body member can include a sharp or pointed tip. In one preferred embodiment, the distal end 6 of the body member has a ramp-like angle. Preferably, the device according to this embodiment can be utilized to make an incision in the body, rather than requiring separate equipment and/or procedures for making the incision site. If the distal end 6 of the body member 2 is used to pierce the body during insertion, at least the distal end 6 is preferably fabricated of a rigid, non-pliable material suitable for piercing the body. Such materials are well known and can include, for example, polyimide and similar materials. In one such preferred embodiment, the distal end 6 of the body member 2 is utilized to pierce the eye for insertion of the controlled delivery device in the interior of the eye.

In another preferred embodiment, the distal end 6 of the body member 2 can be shaped or bent to form a portion (for example, the distal-most portion of the body member) that is parallel to the longitudinal axis. In one embodiment illustrated in FIGS. 3 and 4, for example, the distal end 6 includes a sharp or pointed tip that is parallel to the longitudinal axis. According to this particular embodiment, the tip located at the distal end 6 of the body member is perpendicular to the plane of incision, thus providing a self-starting tip of the device. While these figures illustrate a sharp tip of the body member, it is understood that any suitable configuration of the distal tip can be provided, utilizing the teaching herein.

The body member 2 can be fabricated from a solid material (a material that does not contain a lumen) or a material containing a lumen, as desired. In the embodiment illustrated in FIGS. 1 to 4, for example, the body member 2 is fabricated from a solid material that is shaped into a coil. Alternatively, the body member 2 can be fabricated from a tubular material that includes a lumen. The choice of a solid or lumen-containing material is not critical to the invention and can be determined based upon availability of materials and processing considerations.

When included, the lumen(s) can extend along the length of the body member 2 or only a portion of the length of the body member 2, as desired. In some embodiments, the lumen(s) can serve as a delivery mechanism for delivery of a desired substance to the implantation site. The substance delivered via the lumen can comprise any of the bioactive agents described herein. The substance delivered via the lumen can be the same or different bioactive agent(s) from that included in the coating composition. Further, the substance can be provided in addition to the bioactive agent of the polymeric coating composition, or in place of the bioactive agent. For example, in one embodiment, one or more substances can be delivered via the lumen, and one or more bioactive agents can be provided to the implantation site from the coated composition.

In some embodiments, the lumen can contain a polymeric coated composition as described herein. According to these particular embodiments, the body member of the device can be provided with or without a coating on its external surface. In some such embodiments, the lumen can be utilized to deliver the bioactive agent(s) to the implantation site. For example, the lumen can contain the polymeric coated composition, including first polymer, second polymer, and bioactive agent. According to this particular embodiment, the body member can be provided with a coating on an external surface comprising the first polymer and second polymer only (that is, lacking any bioactive agent). Thus, the bioactive agent is provided to the implantation site in this embodiment principally via the lumen of the body member. In other embodiments, the lumen can include the inventive polymeric coated composition (including first polymer, second polymer, and bioactive agent), and the body member is not provided with a coated composition on its external surface.

The lumen can contain any combination of elements, as desired. For example, in some embodiments, the lumen can include only the substance to be delivered. In other embodiments, the lumen can include the substance to be delivered, as well as the polymeric coated composition. The particular combination of elements to be included in the lumen can be selected depending upon the desired application of the device.

When the lumen is to be provided with a substance and/or polymeric coating composition, the lumen can be filled with the desired substance and/or polymeric coating composition prior to inserting the device into the body, or after the device has been inserted into the body. When it is desired to fill the device with the substance after insertion into the body, a port can be provided near the proximal end 4 of the body member 2 for such purpose. The port is in fluid communication with the lumen(s) of the body member and can also be used for refilling the device with the substance and/or polymeric coating composition after implantation, when desired.

When the device includes a port, the port is preferably designed such that the needle of an injection mechanism (for example, a syringe) can be inserted into the port and the material to be included in the lumen injected by the injection mechanism. Thus, the material can travel through the port and into the lumen(s) of the body member. The port preferably forms a snug seal about the needle of the injection mechanism to prevent leakage of the material out of the port around the injection mechanism and to provide sterile injection of material into the lumen(s). If desired, fittings or collars (not shown), through which an injection mechanism can be inserted and which form a snug seal about the injection mechanism, can be mounted on the port. Upon injection of the material into the delivery device, the needle of the injection mechanism is removed from the port and the port sealed. Sealing can be accomplished by providing a removable cover (not shown) on the port that can be removed for injection of the substance and replaced when the material has been injected. In a preferred embodiment, the port is fabricated of a self-sealing material through which the injection mechanism can be inserted and which seals off automatically when the injection mechanism is removed. Such materials are known and include, for example, silicone rubber, silicone elastomers, polyolefin, and the like.

In further embodiments, when the device includes more than one lumen, the device can include more than one port. For example, each lumen can be in fluid communication with a plurality of ports. These ports are similar to the single port described above. If desired, the lumens and ports can be arranged such that each lumen can be filled with a different material through a corresponding port (for example, each lumen has its own dedicated port). It can be desirable to include more than one lumen when it is desirable to deliver more than one additional material to the implantation site.

In embodiments where it is desired to deliver one or more additional substances to the implantation site via one or more lumens, the individual lumens can include one or more apertures to allow such delivery. In one embodiment, such apertures are provided at the distal end 6 of the device. In other embodiments, the apertures are provided along the length of the body member 2. The number and size of the apertures can vary depending upon the desired rate of delivery of the substance (when provided) and can be readily determined by one of skill in the art. The apertures are preferably designed such that the substance to be delivered is slowly diffused rather than expelled as a fluid stream from the device. For example, when the device is implanted in the eye, it is preferable to deliver the substance through slow diffusion rather than expulsion of the substance as a fluid stream, which can damage the delicate tissues of the eye. In some embodiments, the polymeric coating composition in contact with the body can provide a particular porosity to the substance and can assist in controlling the rate of diffusion of the substance from the lumen. When included in the device, the particular location of the apertures can be situated so as to deliver the substance at a particular location once the device is implanted into the body.

In another embodiment, when the body member 2 includes a lumen for delivery of an additional substance to the implantation site, the material forming the body member 2 can be chosen to be permeable (or semi-permeable) to the substance to be delivered from the lumen. According to this particular embodiment, the material can be chosen depending upon the particular application of the device and the substance to be delivered and can be readily determined by one of skill in the art. Examples of suitable permeable materials include polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers, porous fibers, and the like.

According to these particular embodiments, the material used to fabricate the body member 2 can be chosen to provide a particular rate of delivery of the substance, which can be readily determined by one of skill in the art. Further, the rate of delivery of the substance can be controlled by varying the percentage of the body member 2 formed of the permeable (or semi-permeable) material. Thus, for example, to provide a slower rate of delivery, the body member 2 can be fabricated of 50% or less permeable material. Conversely, for a faster rate of delivery, the body member 2 can be fabricated of greater than 50% of permeable material. When one or more portions of the body member 2, rather than the whole body member 2, is fabricated of a permeable or semi-permeable material, the location of the permeable or semi-permeable material can be situated so as to deliver the substance at a particular location once the device is implanted at the implantation site.

In another embodiment, the lumen of the body member 2 can include impermeable dividers located along the length of the lumen. Thus, the lumen of the body member can contain a plurality of compartments, each of which can be filled with a different substance, as desired. These compartments could be filled prior to insertion through an injection port located, for example, in the side of each compartment. In another embodiment, the device can be filled after it is implanted by providing a plurality of conduits, each conduit in fluid communication with a corresponding compartment. These conduits can be provided within the wall of the body member 2, along the circumference of the body member 2. The substances could then be injected through a plurality of ports, each port in fluid communication with a corresponding conduit. Thus, a substance could be injected into the first compartment just below the cap 8 by a port in the center of the cap 8, which delivers the substance directly into the first compartment. A substance injected into the second port, would flow through conduit and would flow through an aperture in the wall of body member 2 into second compartment, and so on. The substance(s) to be delivered can be delivered to the implantation site via any of the methods described herein for the lumen(s).

In another embodiment, each lumen or compartment (as desired) can be designed for selected "opening" or activation by a laser (via heat or photodisruption). For example, a laser could be used to create apertures in the walls of the desired lumen and/or compartment when the particular substance is to be delivered. As such, release of each substance could be controlled upon demand by an interventionalist. Preferably, when a laser is utilized to create such apertures, the wavelength and temperature are controlled to minimize any effects on the polymeric coating composition.

In preferred embodiments, the body member 2 can be fabricated in a way that further increases the surface area of the body member, preferably without increasing the overall dimensions of the device. For example, in one embodiment, the device can be fabricated of multiple strands of material that are entwined or twisted around each other to form the body member 2 (for example, multiple strands of wire can be twisted around each other to form the body member). According to these particular embodiments, any number of individual strands can be utilized to form the body member, for example, 2, 3, 4, or more strands. The number of individual strands twisted to form the body member can be selected depending upon such factors as, for example, the desired diameter of the material forming the body member and/or the overall body member diameter, the desired flexibility or rigidity of the device during insertion and/or implantation, the size of the implantation, the desired incision size, the material used to form the body member, and the like.

Provision of the polymeric coating composition to the body member according to these embodiments can be achieved in any desirable manner. For example, each individual strand can be provided with a polymeric coating composition prior to twisting the strands to form the body member. Alternatively, the individual, uncoated, strands can be twisted to form the body member, and the formed body member can be provided with the polymeric coating composition.

In another embodiment, the surface area of the body member 2 can be increased by including surface configurations on the body member 2. According to these embodiments, any suitable type of surface configuration can be provided to the body member 2, such as, for example, dimples, pores, raised portions (such as ridges or grooves), indented portions, and the like. Surface configuration can be accomplished by roughening the surface of the material used to fabricate the body member 2. In one such embodiment, the surface of the body member is roughened using mechanical techniques (such as mechanical roughening utilizing such material as 50 μm silica), chemical techniques, etching techniques, or other known methods. In other embodiments, surface configuration can be accomplished by utilizing a porous material to fabricate the body member 2. Examples of porous material are described elsewhere herein. Alternatively, materials can be treated to provide pores in the material, utilizing methods well known in the art. In still further embodiments, surface configuration can be accomplished by fabricating the body member 2 of a machined material, for example, machined metal. The material can be machined to provide any suitable surface configuration as desired, including, for example, dimples, pockets, pores, and the like.

In still further embodiments, increased device surface area can be provided by utilizing a body member configured as a threaded shaft that is tapered or untapered, as desired. Such threaded shaft embodiments are similar to a typical wood screw. The threaded shaft can be fabricated using any suitable techniques, such as molding or machining the threads of the shaft. Further, the threading on the shaft can be a continuous spiral thread that runs continually from the proximal to the distal end of the body member, or the threading can be provided as noncontiguous rings about the body member. Although these particular embodiments can require a larger incision site for implantation of the device in a patient, in some applications, the increased surface area provided by the threaded shaft (discussed in more detail herein) can outweigh the larger incision required.

In preferred embodiments, surface configuration of the body member 2 can provide advantages, such as, for example, increased surface area of the body member for application of the polymeric coating composition, increased durability of the device, increased tenacity of the polymeric coating composition to the body member (for example, by virtue of a roughened surface, increased surface area for adherence, and the like), enhanced removability of the device after a desired treatment duration, and the like.

The body member 2 can include surface configurations along its entire length, or only a portion of the length of the body member, as desired.

As shown in FIG. 1, the body member 2 is preferably cylindrical in shape, with a circular cross-section. However, the cross-sectional shape of the body member 2 is not limited and, for example, can alternatively have square, rectangular, octagonal or other desired cross-sectional shapes.

As shown in FIGS. 1 and 3, a preferred embodiment can include a cap 8 positioned at the proximal end 4 of the body member 2. When included in the device, the cap 8 can assist in stabilizing the device once implanted in the body, thereby providing additional anchoring features of the device. Preferably, the device is inserted into the body through an incision until the cap 8 abuts the incision on the exterior of the body. If desired, the cap 8 can then be sutured to the body at the incision site to further stabilize and prevent the device from moving once it is implanted in its desired location. When the device is implanted in the eye, for example, the device can be inserted into the eye through an incision until the cap 8 abuts the incision. If desired, the cap 8 can then be sutured to the eye, to provide further stabilization as discussed above.

The overall size and shape of the cap 8 is not particularly limited, provided that irritation to the body at the incision site is limited. Preferably, the cap 8 is sized such that it provides a low profile. For example, the dimensions of the cap 8 are preferably selected to provide a small surface area to accomplish such desired features as additional anchoring characteristics of the device, without substantially increasing the overall profile of the device upon implantation. In some embodiments, for example, the cap can be covered by a flap of tissue at the incision site upon implantation, to further reduce potential irritation and/or movement of the device at the implantation and/or incision sites. One illustrative example described in more detail elsewhere herein is the covering of the cap with a scleral flap upon implantation of the device in the eye.

Further, while the cap 8 is illustrated with a circular shape, the cap can be of any shape, for example, circular, rectangular, triangular, square, and the like. In order to minimize irritation to the incision site, the cap preferably has rounded edges. The cap 8 is designed such that it remains outside the implantation site and, as such, the cap 8 is sized so that it will not pass into the implantation site through the incision through which the device is inserted.

As described herein, inclusion of a cap 8 in the device can provide additional anchoring features to the device itself. However, in some embodiments, it can be desirable to further secure the device to provide additional anchoring or securing features at the implantation site. Thus, when desired, the cap 8 can be further designed such that it can be easily sutured or otherwise secured to the surface surrounding the incision and can, for example, contain one or more holes (not shown) through which sutures can pass.

The materials used to fabricate the cap 8 are not particularly limited and include any of the materials previously described for fabrication of the body member 2. Preferably, the materials are insoluble in body fluids and tissues with which the device comes in contact. Further, it is preferred that the cap 8 is fabricated of a material that does not cause irritation to the portion of the body that it contacts (such as the area at and surrounding the incision site). For example, when the device is implanted into the eye, the cap 8 is preferably fabricated from a material that does not cause irritation to the portion of the eye that it contacts. As such, preferred materials for this particular embodiment include, by way of example, various polymers (such as silicone elastomers and rubbers, polyolefins, polyurethanes, acrylates, polycarbonates, polyamides, polyimides, polyesters, polysulfones, and the like), as well as metals (such as those described previously for the body member).

In some embodiments, the cap 8 can be fabricated from the same material as the body member 2. Alternatively, the cap 8 can be fabricated from a material that is different from the body member 2. The cap 8 can be fabricated separately from the body member 2, and subsequently attached to the body member 2, using any suitable attachment mechanism (such as, for example, suitable adhesives or soldering materials). For example, the cap 8 can be fabricated to include an aperture, into which the body member 2 is placed and thereafter soldered, welded, or otherwise attached. In alternative embodiments, the cap 8 and body member 2 are fabricated as a unitary piece, for example, utilizing a mold that includes both components (the body member 2 and cap 8) of the device. The precise method of fabricating the device can be chosen depending upon such factors as availability of materials and equipment for forming the components of the device.

In some embodiments, the cap 8 can be provided with a polymeric coating composition. According to these particular embodiments, the polymeric coating composition provided in connection with the cap 8 can be the same as, or different from, the polymeric coating composition provided in connection with the body member 2. For example, the particular bioactive agent included in the polymeric coating composition for the cap 8 can be varied to provide a desired therapeutic effect at the incision site. Exemplary bioactive agents that could be desirable at the incision site include antimicrobial agents, anti-inflammatory agents, and the like, to reduce or otherwise control reaction of the body at the incision site. It will be readily apparent upon review of this disclosure that the first polymer and second polymer can also be selected for the polymeric coating composition provided in connection with the cap 8, to provide a desired polymeric coating composition specific for the cap, when desired.

In some embodiments, the cap 8 can include a polymeric coated composition that is the same as the polymer coated composition provided in connection with the body member 2. According to these embodiments, the polymeric coating composition can be applied in one step to the entire controlled delivery device (body member and cap), if desired. Alternatively, the polymeric coating composition can be applied to the cap 8 in a separate step, for example, when the cap 8 is manufactured separately, and subsequently attached to the body member 2.

According to the invention, a polymeric coated composition is provided in contact with the body member of the device. Preferably, the polymeric coated composition comprises a first polymer, a second polymer, and a bioactive agent.

The coated composition is provided in contact with at least a portion of the body member of the device. In some embodiments, for example, it can be desirable to provide the coated composition in contact with the entire surface of the body member. Alternatively, the coated composition can be provided on a portion of the body member (such as, for example, an intermediate portion of the body member located between the proximal and distal ends thereof). In some preferred embodiments, for example, it can be desirable to provide the coated composition in contact with a portion of the body member that does not include a sharp distal tip of the body member. This can be desirable, for example, to reduce risk of delamination of the coated composition at the sharp tip and/or to maintain the sharpness of the tip. The amount of the body member that is in contact with the coated composition can be determined by considering such factors as the amount of bioactive agent to be provided at the implantation site, the choice of first polymer and/or second polymer for the coated composition, the characteristics of the implantation site, risk of delamination of the coated composition, and the like. For example, in some embodiments, it can be desirable to provide the coated composition on portions of the body member other than the proximal and distal ends of the device, so as to reduce risk of delamination upon implant and/or explant of the device. Optionally, such delamination can also be minimized, in some embodiments, by providing a stepped coating thickness, such that the coating thickness decreases towards the proximal and/or distal ends of the body member. In still further optional embodiments, the body member can be provided with a coated composition at its distal and/or proximal ends that differs from the composition of the coating at other portions of the body member. One example of such an embodiment includes a body member having a lubricious coating at the distal and/or proximal end of the body member, with a different coated composition in the intermediate portion of the body member that is located between the proximal and distal ends of the body member. Utilizing the concepts described herein, one of skill in the art can determine the amount of body member to be provided in contact with the coated composition, and/or the composition of coated composition provided at one or more distinct regions of the body member, as desired.

Suitable first polymers, second polymers, and bioactive agents for use in preparing coating compositions in accordance with the invention can be prepared using conventional organic synthesis procedures and/or are commercially available from a variety of sources. Preferably, such polymers are either provided in a form suitable for in vivo use in a coating composition, or are purified for such use to a desired extent (for example, by removing impurities) by conventional methods available to those skilled in the art.

A coating composition can be prepared to include a solvent, a combination of complementary polymers (first polymer and second polymer) dissolved in the solvent, and the bioactive agent or agents dispersed in the polymer/solvent mixture. The solvent is preferably one in which the polymers form a true solution. The bioactive agent can either be soluble in the solvent or form a dispersion throughout the solvent. In use, these embodiments do not require any mixing on the part of the user prior to application of the coating composition to the device. In preferred embodiments, the coating composition can provide a one-part system that can be applied to the device in one composition. For example, U.S. Pat. No. 6,214,901 exemplifies the use of tetrahydrofuran (THF) as a solvent. While THF is suitable, and at times preferred for certain coating compositions, other solvents can be used in accordance with the invention as well, including, for example, alcohols (such as methanol, butanol, propanol, isopropanol, and the like), alkanes (such as halogenated or unhalogenated alkanes such as hexane and cyclohexane), amides (such as dimethylformamide), ethers (such as dioxolane), ketones (such as methylketone), aromatic compounds (such as toluene and xylene), acetonitrile, and esters (such as ethyl acetate).

The coated composition is preferably biocompatible, such that it results in no significant induction of inflammation or irritation when implanted in the body. In addition, the coated composition is preferably useful under a broad spectrum of both absolute concentrations and relative concentrations of the polymers. In the context of the previous sentence, the physical characteristics of the coated composition (such as tenacity, durability, flexibility and expandability) will typically be suitable over a broad range of polymer concentrations. Furthermore, the ability of the invention to control the release rates of a variety of bioactive agents can preferably be manipulated by varying the absolute and/or relative concentrations of the polymers and/or the bioactive agent(s).

Turning to the polymeric coating composition itself, in a preferred embodiment, the polymeric coating composition comprises a first polymer, a second polymer, and a bioactive agent. Preferably, the first polymer provides one or more desirable properties, such as compatibility with the second polymer and bioactive agent, hydrophobicity, durability, bioactive agent release characteristics, biocompatibility, molecular weight, and commercial availability. Preferably, the first polymer comprises polyalkyl(meth)acrylate, aromatic poly(meth)acrylate, or a combination of polyalkyl (meth)acrylate and aromatic poly(meth)acrylate.

An example of a suitable polyalkyl(meth)acrylate includes poly(n-butyl)methacrylate. In one preferred embodiment, the polymeric coating composition comprises poly(n-butyl) methacrylate ("pBMA") and poly(ethylene-co-vinyl acetate) copolymers as the second polymer ("pEVA"). This composition has proven useful with absolute polymer concentrations in the range of about 0.05% to about 70% by weight of the coating composition. As used herein "absolute polymer concentration" refers to the total combined concentrations of first polymer and second polymer in the coating composition. In one preferred embodiment, the coating composition comprises polyalkyl(meth)acrylate (such as poly(n-butyl)methacrylate with a weight average molecular weight in the range of about 100 kilodaltons (kD) to about 1000 kD and a pEVA copolymer with a vinyl acetate content in the range of about 10% to about 90% by weight of the pEVA copolymer. In a particularly preferred embodiment, the polymer composition comprises polyalkyl(meth)acrylate (such as poly(n-butyl) methacrylate) with a molecular weight in the range of about 200 kD to about 500 kD and a pEVA copolymer with a vinyl acetate content in the range of about 30% to about 34% by weight. The concentration of the bioactive agent in the polymeric coating composition of this embodiment can be in the range of about 0.01% to about 90% by weight, based upon the weight of the final coating composition.

As used herein "weight average molecular weight" or $M_w$, is an absolute method of measuring molecular weight and is particularly useful for measuring the molecular weight of a polymer preparation. The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

Coating compositions including aromatic poly(meth)acrylates can provide unexpected advantages in certain embodiments. Such advantages relate, for instance, to the ability to provide coatings having different characteristics (such as different solubility characteristics) than other coatings (for example, those that include a polyalkyl(meth)acrylate polymer), while maintaining a desired combination of other properties. Without intending to be bound by a particular theory, it appears that the increased solubility (particularly in more polar solvents) that is provided by an aromatic, rather than an alkyl poly(meth)acrylate of this invention, permits the use of poly(ethylene-co-vinyl acetate) polymers that are themselves more polar (for example, having significantly greater vinyl acetate concentrations) than those typically preferred for use with the polyalkyl(meth)acrylates.

Examples of suitable aromatic poly(meth)acrylates include polyaryl(meth)acrylates, polyaralkyl(meth)acrylates, and polyaryloxyalkyl(meth)acrylates, in particular those with aryl groups having from six to sixteen carbon atoms and weight average molecular weights in the range of about 50 kD to about 900 kD. Preferred aromatic poly(meth) acrylates include those compounds wherein at least one carbon chain and at least one aromatic ring are combined with acrylic groups (typically esters). For example, a polyaralkyl (meth)acrylate or polyarylalkyl(meth)acrylate can be made from aromatic esters derived from alcohols also containing aromatic moieties.

Examples of polyaryl(meth)acrylates include poly-9-anthracenylmethacrylate, polychlorophenylacrylate, polymethacryloxy-2-hydroxybenzophenone, polymethacryloxybenzotriazole, polynaphthylacrylate, polynapthylmethacrylate, poly-4-nitrophenylacrylate, polypentachloroacrylate, polypentabromoacrylate, polypentafluoroacrylate, polypentachloromethacrylate, polypentabromomethacrylate, polypentafluoromethacrylate, polyphenylacrylate, and polyphenylmethacrylate.

Examples of polyaralkyl(meth)acrylates include polybenzylacrylate, polybenzylmethacrylate, poly-2-phenethylacrylate, poly-2-phenethylmethacrylate, and poly-1-pyrenylmethylmethacrylate.

Examples of polyaryloxyalkyl(meth)acrylates include polyphenoxyethylacrylate, polyphenoxyethylmethacrylate, and polyethyleneglycolphenylether acrylates and polyethyleneglycolphenylether methacrylates with varying polyethyleneglycol molecular weights.

The second polymer of the polymeric coating composition preferably provides one or more desirable properties, such as compatibility with the first polymer and bioactive agent, hydrophobicity, durability, bioactive agent release characteristics, biocompatibility, molecular weight, and commercial availability, particularly when used in admixture with the first polymer.

Examples of suitable second polymers are commercially available and include poly(ethylene-co-vinyl acetate) having vinyl acetate concentrations in the range of about 10% to about 90% by weight of the pEVA copolymer, or in the range of about 20% to about 60% by weight of the pEVA copolymer, or in the range of about 30% to about 34% by weight of the pEVA copolymer. Poly(ethylene-co-vinyl acetate) co-polymers having lower percent vinyl acetate can become increasingly insoluble in typical solvents, such as THF, toluene, and the like. The second polymer can be obtained commercially in the form of beads, pellets, granules, and the like.

A particularly preferred coating composition in accordance with the invention comprises polyalkyl(meth)acrylates (for example, poly(n-butyl)methacrylate) or aromatic poly(meth)acrylates (for example, polybenzyl(meth)acrylates) and poly(ethylene-co-vinyl acetate) copolymers. This particular composition has proven useful with absolute polymer concentrations (as defined herein) in the range of about 0.05% to about 70% by weight of the total coating composition, more preferably in the range of about 0.25% to about 10% by weight of the total coating composition.

In one preferred embodiment, the polymer composition includes a first polymer with a weight average molecular weight in the range of about 100 kD to about 500 kD, and a pEVA copolymer with a vinyl acetate content in the range of about 10% to about 90% by weight, and more preferably in the range of about 20% to about 60% by weight. In a particularly preferred embodiment, the polymer composition includes a first polymer with a weight average molecular weight in the range of about 200 kD to about 500 kD, and a pEVA copolymer with a vinyl acetate content in the range of about 30% to about 34% by weight.

In preferred embodiments, the coating composition comprises a bioactive agent. For purposes of the description herein, reference will be made to "bioactive agent," but it is understood that the use of the singular term does not limit the application of bioactive agents contemplated, and any number of bioactive agents can be provided using the teaching herein. As used herein, "bioactive agent" refers to an agent that affects physiology of biological tissue. Bioactive agents useful according to the invention include virtually any substance that possess desirable therapeutic characteristics for application to the implantation site.

Exemplary bioactive agents include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 13-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); mydriatics (such as atropinsurface, cyclopentolate, homatropine, scopolamine, tropicamide, eucatropine, hydroxyamphetamine); sympathomimetics (such as epinephrine); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); beta adrenergic blockers (such as timolol maleate, levobunolol HCl, betaxolol HCl); immunosuppressive agents, growth hormone antagonists, growth factors (such as epidermal growth factor, fibroblast growth factor, platelet derived growth factor, transforming growth factor beta, somatotropin, fibronectin); carbonic anhydrase inhibitors (such as dichlorophenamide, acetazolamide, methazolamide); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

The particular bioactive agent, or combination of bioactive agents, can be selected depending upon one or more of the following factors: the application of the controlled delivery device, the medical condition to be treated, the anticipated duration of treatment, characteristics of the implantation site, the number and type of bioactive agents to be utilized, and the like.

The concentration of the bioactive agent in the coating composition can be provided in the range of about 0.01% to about 90% by weight, based on the weight of the final coating composition. Preferably, the bioactive active agent is present in the coating composition in an amount in the range of about 75% by weight or less, preferably about 50% by weight or less. The amount of bioactive agent in the coating composition can be in the range of about 1 µg to about 10 mg, or about 100 µg to about 1500 µg, or about 300 µg to about 1000 µg.

The coating composition can be applied to the controlled delivery device using any suitable methods. For example, the coating composition can be applied by dipping, spraying, and other common methods for applying coating compositions to implantable devices. The suitability of the coating composition for use on a particular material, and in turn, the suitability of the coated composition, can be evaluated by those skilled in the art, given the present description.

In some aspects, the coating composition can be applied to the controlled delivery device utilizing an ultrasonic spray head as described in Example 2. As described in Example 2, the cap of the controlled delivery device can be supported with a pin vice during the coating procedure.

In some embodiments, the surface of the body member can be pretreated prior to provision of the coating composition. Any suitable surface pretreatment commonly employed in coating implantable devices can be utilized in accordance with the invention, including, for example, treatment with silane, polyurethane, parylene, and the like. For example, Parylene C (commercially available from Union Carbide Corporation), one of the three primary variants of parylene, can be used to create a polymer layer on the surface of a medical device. Parylene C is a para-xylylene containing a substituted chlorine atom, which can be coated by delivering it in a vacuum environment at low pressure as a gaseous polymerizable monomer. The monomer condenses and polymerizes on substrates at room temperature, forming a matrix on the surface of the medical device. The coating thickness can be controlled by pressure, temperature, and the amount of monomer used. The parylene coating provides an inert, non-reactive barrier.

In some embodiments, the coated composition comprises at least two layers, wherein each layer comprises the same coated composition, or different coated compositions. In one such embodiment, a first layer having either bioactive agent alone, or bioactive agent(s) together with one or more of the polymers (first polymer and/or second polymer) is applied, after which one or more additional layers are applied, each with or without bioactive agent. These different layers, in turn, can cooperate in the resultant composite coating to provide an overall release profile having certain desired characteristics, and is particularly preferred for use with bioactive agents having high molecular weight. According to the invention, the composition of individual layers of the coating can include any one or more of the following: one or more bioactive agents, the first polymer, and/or the second polymer, as desired.

Preferably, the coating composition is applied to the body member of the controlled delivery device surface in one or more applications. The method of applying the coating composition to the body member is typically governed by such factors as the geometry of the device and other process considerations. The coated composition can be subsequently dried by evaporation of the solvent. The drying process can be performed at any suitable temperature, (for example, room temperature or elevated temperature), and optionally with the assistance of vacuum.

In some preferred embodiments, the coating composition is applied to the body member under conditions of controlled relative humidity. As used herein, "relative humidity" is the ratio of the water vapor pressure (or water vapor content) to the saturation vapor pressure (or the maximum vapor content) at a given temperature of the air. The saturation vapor pressure in the air varies with air temperature: the higher the temperature, the more water vapor it can hold. When saturated, the relative humidity in the air is 100% relative humidity. According to some embodiments of the invention, the coating composition can be applied to the body member under conditions of increased or decreased relative humidity as compared to ambient humidity.

According to the invention, humidity can be controlled in any suitable manner, including at the time of preparing and/or applying the coating composition to the body member. For example, when humidity is controlled at the time of preparing the coating composition, the water content of the coating composition can be adjusted, before and/or after the coating composition is applied to the body member. When humidity is controlled at the time of applying the coating composition, the coating composition can be applied to the body member in a confined chamber or area adapted to provide a relative humidity that differs from ambient humidity. Generally, it has been found that applying coating compositions under conditions of increased humidity will typically accelerate release of the bioactive agent, while applying coating compositions under conditions of decreasing humidity levels will tend to decelerate release of the bioactive agent. As contemplated in the invention, even ambient humidity can be considered "controlled" humidity if it has been correlated with and determined to provide a corresponding controlled release of the bioactive agent.

Moreover, and particularly when coating a plurality of coating compositions onto the body member of the controlled delivery device to provide the final coated composition, humidity can be controlled in different ways (for example, using a controlled environment as compared to adjusting the water content of the coating composition) and/or at different levels to provide a desired release profile for the resulting coated composition. As described previously, a coated composition can be provided using a plurality of individual steps or layers of coating composition, including, for instance, an initial layer having only bioactive agent (or bioactive agent with one or both polymers), over which is coated one or more additional layers containing suitable combinations of bioactive agent, first polymer, and/or second polymer, the combined result of which is to provide a coated composition of the invention.

Thus, in preferred embodiments, the invention provides the ability to reproducibly control the release of a bioactive agent from a controlled delivery device.

In some embodiments, a plurality of coating compositions and corresponding coating steps can be employed, each with its own controlled humidity (when desired), in order to provide a desired combination of layers, each with its corresponding release profile. Those skilled in the art will appreciate the manner in which the combined effect of these various layers can be used and optimized to achieve various effects in vivo.

In yet another embodiment, the desired release rate of the bioactive agent from the coated composition can be selected by applying the coating composition to surfaces at a plurality of different humidity levels, and evaluating the corresponding release profiles to determine a controlled humidity level corresponding to a desired profile. In one such embodiment, for instance, the coating composition is applied to the device under relative humidity controlled at a level in the range of about 0% to about 95% relative humidity (at a given temperature, in the range of about 15° C. to about 30° C.), and more preferably in the range of about 0% to about 50% relative humidity. Without intending to be bound by a particular theory, it has been found that potential differences in the ambient humidity, as between coating runs at the same location, and/or as between different coating locations, can vary significantly, and in a manner that might affect such properties as the release of the bioactive agent. By using a controlled humidity, the invention can provide a coated composition that displays significantly more controllable and reproducible release characteristics.

The coating composition of the invention can be provided in any suitable form, for example, in the form of a true solution, or fluid or paste-like emulsion, mixture, dispersion, or blend. In turn, the coated composition will generally result from the removal of solvents or other volatile components and/or other physical-chemical actions (for example, heating or illumination) affecting the coated composition in situ upon the controlled delivery device surface.

The overall weight of the coated composition upon the surface of the controlled delivery device is typically not critical. The weight of the coated composition attributable to the bioactive agent can be in the range of about 1 μg to about 10 mg of bioactive agent per $cm^2$ of the surface area of the controlled delivery device. In some embodiments, the surface area can comprise all or a portion of the body member 2 of the device. In alternative embodiments, the surface area can comprise the body member 2 and the cap 8 of the device. Preferably, the weight of the coated composition attributable to the bioactive agent is in the range of about 0.01 mg to about 10 mg of bioactive agent per $cm^2$ of the surface area of the controlled delivery device. This quantity of bioactive agent is generally effective to provide adequate therapeutic effect under physiological conditions. As used herein, the surface area is the macroscopic surface area of the device.

In preferred embodiments, the final coating thickness of the coated composition on the controlled delivery device will typically be in the range of about 0.1 µm to about 100 µm, or in the range of about 5 µm to about 60 µm. This level of coating thickness is generally effective to provide a therapeutically effective amount of bioactive agent to the implantation site under physiological conditions. The final coating thickness can be varied, and at times be outside the preferred ranges identified herein, depending upon such factors as the total amount of bioactive agent to be included in the coated composition, the type of bioactive agent, the number of bioactive agents to be included, the treatment course, the implantation site, and the like.

Thickness of the coated composition on the controlled delivery device can be assessed using any suitable techniques. For example, portions of the coated composition can be delaminated by freezing the coated controlled delivery device, for example, utilizing liquid nitrogen. The thickness at the edge of a delaminated portion can then be measured by optical microscopy. Other visualization techniques known in the art can also be utilized, such as microscopy techniques suitable for visualization of coatings having the thickness described herein of the invention.

In preferred embodiments, the controlled delivery device is sterilized utilizing common sterilization techniques, prior to implantation into the body. Sterilization can be accomplished, for example, utilizing ethylene oxide or gamma sterilization, as desired. In preferred embodiments, sterilization techniques utilized do not affect the polymeric coated composition (for example, by affecting release of the bioactive agent, stability of the coating, and the like).

According to the invention, the controlled delivery device preferably provides the ability to deliver one or more bioactive agents in a controlled release manner. As used herein, "controlled release" refers to release of a compound (for example, a bioactive agent) into a patient's body at a desired dosage (including dosage rate and total dosage) and duration of treatment. For example, the particular composition of the coating composition (including the amounts and ratios of the individual components of the coating composition) can be modified to achieve a desired release profile (amount of bioactive agent released from the coating composition per unit time) of the bioactive agent. While not intending to be bound by one particular theory, the release kinetics of the bioactive agent in vivo are thought to generally include both a short term ("burst") release component, within the order of minutes to hours or less after implantation of the device, and a longer term release component, which can range from on the order of hours to days or even months of useful release. As used herein, the acceleration or deceleration of bioactive agent release can include either or both of these release kinetics components.

The desired release profile of the bioactive agent can depend upon such factors as the particular bioactive agent selected, the number of individual bioactive agents to be provided to the implantation site, the therapeutic effect to be achieved, the duration of the implant in the body, and other factors known to those skilled in the art.

The ability to provide controlled release of a bioactive agent at an implantation site can provide many advantages. For example, the controlled delivery device can be maintained at an implantation site for any desired amount of time, and the release kinetics of the bioactive agent can be adjusted to deliver the total amount of bioactive agent, at the desired rate, to achieve a desired therapeutic effect. In some embodiments, the ability to provide controlled release of bioactive agent at the implantation site allows implantation of only one device, which can be maintained in place until the desired therapeutic effect is achieved, without need to remove the device and replace the device with a new supply of bioactive agent. Preferably, some embodiments of the invention avoid the need to refill a reservoir of bioactive agent at the implantation site. In some embodiments, the controlled delivery device can avoid the need for systemic application of bioactive agents, which can harm other tissues of the body.

The controlled delivery device can be utilized to deliver any desired bioactive agent or combination of bioactive agents to the eye, such as the bioactive agents described herein. The amount of bioactive agent(s) delivered over time is preferably within the therapeutic level, and below the toxic level. For example, a preferred target dosage for triamcinolone acetonide for use in treating diseases or disorders of the eye is preferably in the range of about 0.5 µg/day to about 2 µg per day. Preferably, the treatment course is greater than 6 months, more preferably greater than one year. Thus, in preferred embodiments, the bioactive agent is released from the coated composition in a therapeutically effective amount for a period of 6 months or more, or 9 months or more, or 12 months or more, or 36 months or more, when implanted in a patient.

Preferred embodiments of the invention provide a controlled delivery device that can release bioactive agent at a constant rate over extended periods of time. Moreover, the controlled delivery device preferably provides the ability to control the rate of release of bioactive agent by altering the formulation of the coating composition (for example, by providing the first polymer and second polymer in different relative amounts, and/or by altering the amount of bioactive agent included in the coating composition). As illustrated in the Examples, preferred coated compositions can provide release of a bioactive agent in a reproducible manner, for varying time periods, over a range of release rates. In the Examples, coating compositions having varying amounts of poly(ethylene-co-vinyl acetate) relative to the amount of poly(n-butyl)methacrylate, and a constant amount of a bioactive agent, were prepared and coated onto stainless steel substrates. The release rates of bioactive agent from the coated composition were determined in PBS utilizing the Elution Assay described herein. Results illustrated that the bioactive agent could be released from the coated composition for surprisingly long periods of time in vitro. Moreover, the coating compositions could be formulated to provide substantially linear release rates. Based upon the observed release rates in vitro, it is expected that in vivo release rates will be higher than those in PBS. See Jaffe et al., supra. Differences in release rates were observed among the coated compositions, which relate to differences in polymer composition of the coated compositions. Thus, in preferred embodiments, the polymer composition of the coating compositions can be manipulated to control the release rate of the bioactive agent.

Figure 6:
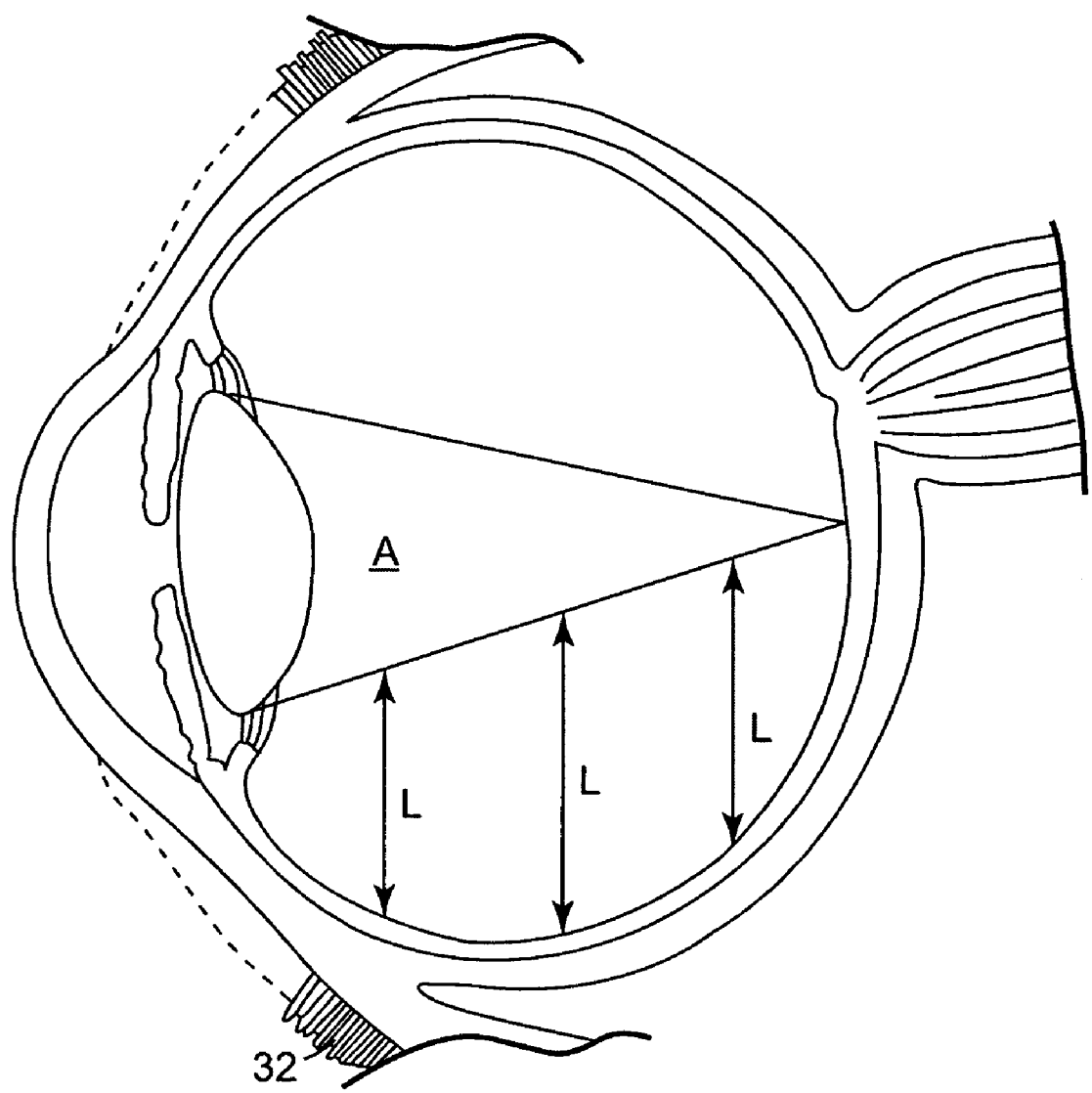
FIG. 6 is a cross-sectional view of an eye illustrating the central visual field "A" of the eye.

Use of the controlled delivery device can be further understood from the following discussion relating to a method for controlled release of a bioactive agent to the eye and with reference to FIGS. 5 and 6. However, it will be understood that the principles described below can be applied to any implantation site within a patient's body.

In accordance with the invention, the controlled delivery device is fabricated, utilizing the teaching herein, in preparation for the surgical procedure. An incision in the body is made to provide access to the implantation site. For example, when used to deliver bioactive agent to the eye, a sclerotomy is created for insertion of the controlled delivery device. Conventional techniques can be used for the creation of the sclerotomy. Such techniques include the dissection of the conjunctiva 32 and the creation of pars plana scleral incisions through the sclera 28. As shown in FIGS. 5 and 6, the dissection of the conjunctiva 32 typically involves pulling back the conjunctiva 32 about the eye so as to expose large areas of the sclera 28, and the clipping or securing of the conjunctiva 32 in that pulled back state (the normal position of the conjunctiva is shown in phantom). In other words, the sclera 28 is exposed only in the areas where the pars plana scleral incisions are to be made. Surgical instruments used in the procedure are then passed through these incisions. Thus, the incisions should be made large enough to accommodate the instruments required for the procedure.

Alternatively, the creation of the sclerotomy can be accomplished by use of an alignment device and method, such as that described in U.S. patent application Ser. No. 09/523,767, that enables sutureless surgical methods and devices thereof. In particular, such methods and devices do not require the use of sutures to seal the openings through which instruments are inserted. The alignment devices are inserted through the conjunctiva and sclera to form one or more entry apertures. Preferably, the alignment devices are metal or polyimide cannulas through which the surgical instruments used in the procedure are inserted into the eye.

In further embodiments, the device can be implanted directly through a self-starting transconjunctival trans-scleral "needle stick." For example, the body member 2 of the device can include a sharp tip 10, such as that illustrated in FIG. 3. According to this embodiment, the sharp tip 10 can be utilized to pierce the body and thereby create the incision site and access to the implantation site. In this case, no conjunctival surgery or extraneous alignment device is necessary.

In further embodiments, the conjunctival tissue can be dissected to expose a portion of the pars plana region, and a needlestick can be made into the sclera in the exposed region. A self-starting coil that includes a sharp tip is then inserted through the pars plana at the site of the needlestick, and the coil is rotated through the sclera until the cap of the device abuts the sclera. In some preferred embodiments, the needlestick is smaller than the diameter of the material forming the body member of the implantable device (for example, a 30-gauge needlestick can be used with an implantable device having a body member with a diameter of 0.5 mm or less). The conjunctival tissue is then pulled over the cap, to provide a flap or "seal" over the device, thus minimizing irritation of the implantation site, foreign body sensation, and the like. Optionally, the conjunctival tissue can be further secured by a single suture (in preferred embodiments, a biodegradable suture).

In some embodiments, it can be preferable to create an incision site that is slightly larger than the dimensions of the proximal portion of the body member. For example, when the device includes a cap 8 and is implanted into the eye, it can be preferable to create an incision that is larger than the largest diameter of the cap 8, such that the cap sits below the outer surface of the sclera. For example, a partial incision in the sclera can be made to create a scleral flap. Once the device has been implanted, and the cap 8 is placed so that it abuts the incision site, the scleral flap can be folded back over the device, thus providing a covering over the cap. Alternatively, when the proximal end of the body member does not include a cap 8, a flap-like cover can still be utilized to cover the proximal end of the device, in accordance with the description above. Preferably, these embodiments minimize the contact of the proximal end (for example, the cap 8) of the device with other body tissues, thereby reducing such risks as irritation of body tissues, and/or translation of movement of the eye to the device, thereby potentially damaging eye tissues. This can provide one or more advantages, such as reduced tendency for movement of the eye to be translated to the controlled delivery device, since the proximal end of the device will not be sitting at the surface of the eye and thus in contact with other body tissues; and reduced irritation of surrounding tissues.

The body member 2 is then inserted into the eye. For example, in embodiments wherein the body member 2 has a coil shape, the body member 2 is inserted into the eye by rotating or twisting the body member 2 into the eye until the cap 8 abuts the outer surface of the eye. In embodiments wherein the body member 2 is fabricated of a shape memory material, the shape memory material is first cooled to a temperature at which the martensite phase is stable and the device is deformed, for example, into a linear shape. The device is then inserted into the eye. To return the device to its memory shape, the device is left unrestrained and is simply allowed to reach a temperature (for example, by heating the device) above the martensite phase temperature. For example, the shape memory material can be heated by a laser to return the device to a temperature above the martensite phase temperature. The shape memory material can also be selected such that the martensite phase temperature is below body temperature so that the material is simply cooled to below body temperature, deformed to a linear shape, and inserted into the eye. Then, as the material warms up within the eye to body temperature, the device can return to its remembered shape. As discussed herein, when laser application is utilized, conditions are preferably controlled to maintain such parameters as wavelength and temperature, to minimize adverse effect on the polymeric coated composition.

FIG. 5 illustrates a controlled delivery device according to one embodiment of the invention that is implanted in the eye. When implanted into the eye, it is desirable to limit the length L of controlled delivery devices to prevent the controlled delivery device from entering the central visual field A (see FIG. 6). If the implant enters the central visual field A, this can result in blind spots in the patient's vision and can increase the risk of damage to the retinal tissue and lens capsule. Thus, for example, when the controlled delivery device is inserted at the pars plana (as shown in FIG. 5), the distance from the implantation site on the pars plana to the central visual field A is preferably less than about 1 cm.

Optionally, after the device is implanted into the eye, the cap 8 can then be sutured or otherwise secured to the sclera to maintain the controlled delivery device in place. In preferred embodiments, no further manipulation of the device is required for delivery of one or more bioactive agents to the interior of the eye. The conjunctiva can be adjusted to cover the cap 8 of the device, when desired, and the surgical procedure is completed.

In other embodiments, when a lumen is included in the device for delivery of one or more additional substances to the interior of the eye, further steps can be included as follows. If a cover is used to close the port(s), it is removed at this time, and if used, a collar for providing a snug fit about the injection mechanism (such as a syringe) is provided. The injection mechanism is then connected with the port(s) for injection of one or more substances to the controlled delivery device. If the port(s) are composed of an self-sealing material through which the needle of an injection mechanism can be inserted and which seals off automatically when the injection mechanism is removed, the injection mechanism is simply inserted through the port and the substance injected. Following injection, the conjunctiva can be adjusted to cover the cap 8 of the device, if desired.

The controlled delivery device of the invention can be used to deliver one or more bioactive agents to the eye for the treatment of a variety of ocular conditions such as, for example, retinal detachment; occlusions; proliferative retinopathy; proliferative vitreoretinopathy; diabetic retinopathy; inflammations such as uveitis, choroiditis, and retinitis; degenerative disease (such as age-related macular degeneration, also referred to as AMD); vascular diseases; and various tumors including neoplasms. In yet further embodiments, the controlled delivery device can be used post-operatively, for example, as a treatment to reduce or avoid potential complications that can arise from ocular surgery. In one such embodiment, the controlled delivery device can be provided to a patient after cataract surgical procedures, to assist in managing (for example, reducing or avoiding) post-operative inflammation.

In some applications, additives can further be included with the bioactive agent and/or additional substance to be delivered to the implantation site. Examples of suitable additives include, but are not limited to, water, saline, dextrose, carriers, preservatives, stabilizing agents, wetting agents, emulsifying agents, excipients, and the like.

Once the bioactive agent has been delivered to the implantation site, the controlled delivery device can be removed if the required therapeutically effective amount of bioactive agent has been delivered for treatment of the condition.

The following examples illustrate the present invention without, however, limiting the same thereto.

EXAMPLES

Test Methods

The suitability of particular coated compositions for in vivo use can be determined by one or more of a variety of methods, including the Durability Test and Elution Assay. Examples of each test are described herein.

Sample Preparation

One-millimeter diameter stainless steel wires (for example, 316 L grade) were cut into 2-centimeter lengths. The wire segments were treated with a Parylene C coating composition (Union Carbide Corporation), as described herein. The wire segments were weighed on a micro-balance.

Coating compositions were prepared at a range of concentrations in an appropriate solvent, in the manner described herein. The coating mixtures were applied to respective wires, or portions thereof, by dipping or spraying, and the coated wires were allowed to dry by solvent evaporation. The coated wires were then re-weighed. From this weight, the mass of the coatings was calculated, which in turn permitted the mass of the coated polymer(s) and bioactive agent(s) to be determined.

The durability of the coated composition was determined in the following manner.

Durability Test

The Durability Test utilized was as follows. Coated devices were prepared as described above. The coated devices were mounted to an insertion tool that firmly engages the cap of the device while avoiding mechanical contact with the coated portion of the device. The devices included a distal sharp tip that was utilized to pass through the conjunctiva and sclera and into the interior of the eye. Cadaveric porcine eyes were obtained, and the distal sharp tip was utilized to place the devices into the eye until the cap of the device was flush with the sclera.

After implantation, the coated devices were immediately removed, utilizing the insertion device used for implantation. Devices were carefully cleaned without the use of solvents (deionized water was used to remove any tissue adhering to the device surface). The devices were then analyzed for surface coating defects (such as delamination of the coating) under light microscopy.

Elution Assay

Any suitable Elution Assay can be used to determine the extent and/or rate of bioactive agent release from the coated composition under physiological conditions. In general, it is desirable that less than 50% of the total quantity of the drug to be released is released in the first 24 hours after introduction into physiological conditions. It is frequently desirable for quantities of bioactive agent to be released for a duration of at least 30 days. After all of the bioactive agent has been released, SEM evaluation should reveal an intact coating.

The Elution Assay utilized herein was as follows. Phosphate buffered saline (PBS, 10 mM phosphate, 150 mM NaCl, pH 7.4, aqueous solution) was pipetted in an amount of 3 ml to 10 ml into an amber vial with a Teflon™ lined cap. A wire or coil treated with the coating composition was immersed into the PBS. A stir bar was placed into the vial and the cap was screwed tightly onto the vial. The PBS was stirred with the use of a stir plate, and the temperature of the PBS was maintained at 37° C. with the use of a water bath. The sampling times were chosen based upon the expected or desired elution rate. At the sampling time point, the wire or coil was removed from the vial and placed into a new vial containing fresh PBS. A UV/Vis spectrophotometer was used to determine the concentration of the drug in the PBS solution that previously contained the wire or coil treated with the coating composition. The cumulative amount of drug eluted versus time was plotted to obtain an elution profile.

At the conclusion of the Elution Assay, the wire or coil was washed with water, dried and re-weighed. Correlation between the percent bioactive agent eluted and the percent weight loss of the coated composition was verified.

When desired, the coating can also be evaluated by measuring the coating thickness (for example, using a Minitest 4100 thickness gauge), and the coating quality (such as roughness, smoothness, evenness, and the like) can be analyzed by SEM analysis.

Nomenclature

The following abbreviations are used in the examples:

pEVA poly(ethylene-co-vinyl acetate) (SurModics, Inc., Eden Prairie, Minn.)

PBMA poly(n-butyl)methacrylate (SurModics, Inc., Eden Prairie, Minn.)

TA triamcinolone acetonide (Sigma-Aldrich Chemical, St. Louis, Mo.)

In the following examples, the compositional details of each coating composition are summarized as a ratio of the weight percentages of polymers used to create the coating composition. For example, a coating composition designated TA/pEVA/PBMA (50/49/1) is made by providing, on a relative basis, 50 parts by weight triamcinolone acetonide, 49 parts by weight poly(ethylene-co-vinyl acetate), and 1 part by weight of poly(n-butyl)methacrylate.

Example 1

Release of Triamcinolone Acetonide from Stainless Steel Wires

Three different polymer solutions were prepared in tetrahydrofuran (THF) in the manner provided below in order to provide coating compositions in the form of a one-part system. The three solutions contained varying amounts of poly (ethylene-co-vinyl acetate), with a vinyl acetate content of 33% (w/w), relative to the amount of poly(n-butyl)methacrylate, with an approximate weight average molecular weight of 337 kD. Each of the three solutions contained a constant amount of triamcinolone acetonide relative to the total polymer weight.

The coating compositions were prepared as follows. The polymers were initially added to the THF and dissolved overnight while mixing on a shaker at 200 revolutions per minute (rpm) at room temperature (approximately 20° C. to 22° C.). After dissolution of the polymer, the triamcinolone acetonide was added, and the mixture was placed back on the shaker at 100 rpm for 1 hour, to form the one-part coating composition. The compositions prepared are summarized below in Table I:

TABLE I

Coating Compositions applied to wire surfaces.

| Coating | Composition | Parts by weight (pbw) | Weight of Coating Composition (µg) |
|---|---|---|---|
| Coating 1a | TA/pEVA/PBMA | 50/49/1 | 1222 |
| Coating 1b | TA/pEVA/PBMA | 50/36/14 | 1266 |
| Coating 1c | TA/pEVA/PBMA | 50/15/35 | 1204 |

Stainless steel wire samples were prepared for coating as follows. The stainless steel wire was cleaned by soaking in a 6% (by volume) solution of ENPREP-160SE (Cat. # 2108-100, Enthone-OMI, Inc., West Haven, Conn.) in deionized water for 1 hour. After soaking, the parts were then rinsed several times with deionized water. After rinsing, the stainless steel wire was soaked for 1 hour at room temperature in 0.5% (by volume) methacryloxypropyltrimethoxy silane (Cat.# M6514, Sigma Aldrich, St. Louis, Mo.) made in a 50% (by volume) solution of deionized water and isopropyl alcohol. The stainless steel wires were allowed to drain and air dry. The dried wires were then placed in a 100° C. oven for 1 hour.

After oven-drying, the stainless steel wires were placed in a parylene coating reactor (PDS 2010 LABCOTER™ 2, Specialty Coating Systems, Indianapolis, Ind.) and coated with 2 g of Parylene C (Specialty Coating Systems, Indianapolis, Ind.) by following the operating instructions for the LABCOTER™ system. The resulting Parylene C coating was approximately 1-2 µm thickness.

Solutions for Coatings 1a, 1b, and 1c were sprayed onto the Parylene C treated wires using an IVEK sprayer (IVEK Dispenser 2000, IVEK Corp., North Springfield, Vt.) mounting a nozzle with a 1.0 mm (0.04 inch) diameter orifice and pressurized at 421.84 g/cm$^2$ (6 psi). The distance from the nozzle to the wire surface during coating application was 5 to 5.5 cm. A coating application consisted of spraying 40 µl of the coating solution back and forth on the wire for 7 seconds. The spraying process of the coating was repeated until the amount of TA on the wire equaled the amount of TA listed for Coatings 1a, 1b, and 1c seen in FIG. 7. The coating compositions on the wire were dried by evaporation of solvent, approximately 8-10 hours, at room temperature (approximately 20° C. to 22° C.). After drying, the coated wires were re-weighed. From this weight, the mass of the coating was calculated, which in turn permitted the mass of the coated polymer(s) and bioactive agent to be determined.

The coated wires were then subjected to the Elution Assay described above. Results of the Elution Assay for each coating composition are illustrated in FIG. 7.

The release rates of the coatings were determined for greater than 175 days. For Coating 1c, the calculated release rate was 0.5 µg/day between days 51 and 456, and the release rate was linear over the duration of the experiment. For Coating 1a, the calculated release rate was 4.2 µg/day between days 14 and 79, and for Coating 1b, the calculated linear release rate was 1.2 µg/day between days 84 and 337. Utilizing these release rates, it was calculated that Coating 1c would be released from the coated composition into PBS (assuming 100% release of TA) for a period exceeding 3 years.

Figure 7:
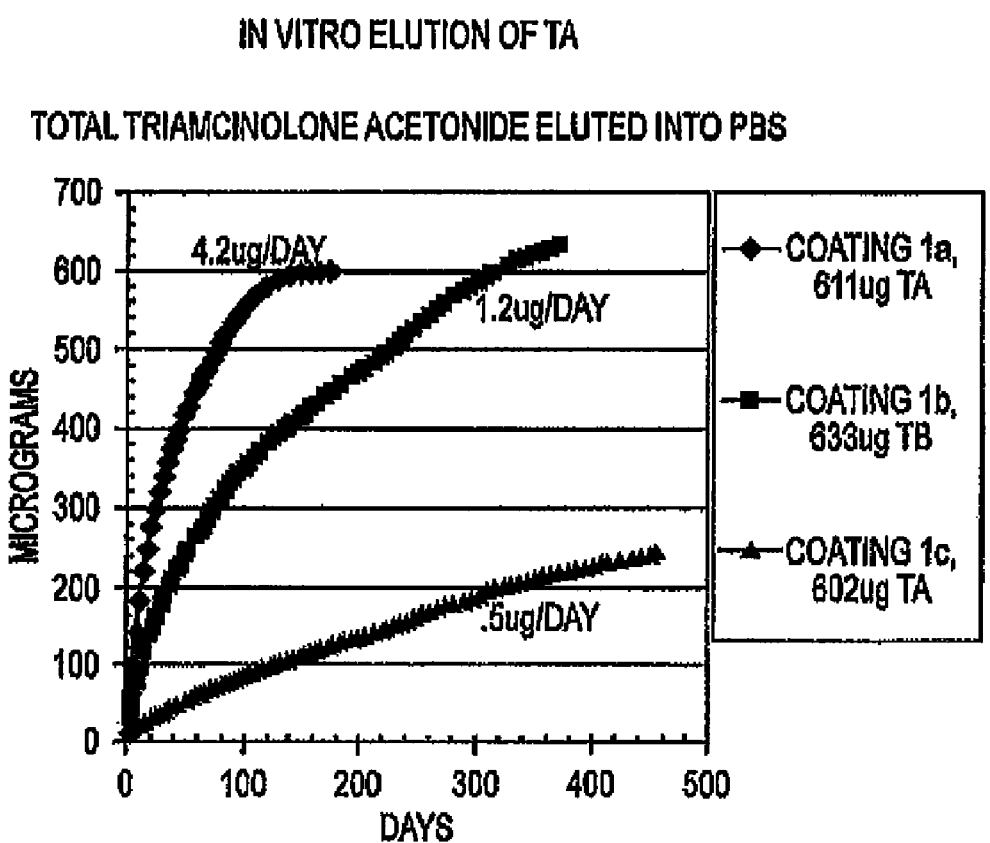
FIG. 7 is a graph showing in vitro elution of triamcinolone acetonide (TA) into phosphate buffered saline (PBS) for the coated wires prepared and tested as described in Example 1.

As shown in FIG. 7, Coating 1a included an initial loading of 611 µg of TA, and 600 µg of the bioactive agent was released within 190 days. Coating 1b included an initial loading of 633 µg of TA, and 631 µg of the bioactive agent was released within 372 days. Coating 1c included an initial loading of 602 µg of TA, and 240 µg of the bioactive agent was released within 456 days.

Results indicate that a bioactive agent, in this case, triamcinolone acetonide, was predicted to elute from a coated composition according to the invention for surprisingly long periods of time in vitro (over three years). Further, the coating composition can provide a substantially linear release rate over time. Moreover, as the results indicate, the coated composition can be varied, for example, by varying the weight ratio of the first polymer and second polymer, to control the elution rate of a bioactive agent, such as triamcinolone acetonide, as desired. Thus, a treatment course can be identified by an interventionalist, and the polymeric coating composition according to the invention can be formulated to provide a controlled release profile to achieve the designated treatment course. As described in more detail herein, the release profile can be further controlled by controlling humidity conditions of the coating composition.

At the conclusion of the Elution Assay, the wire was washed with water, dried and re-weighed. Pre- and post-elution data for coated compositions 1a and 1b are provided in Table II below:

TABLE II

Elution Data for Coated Compositions 1a and 1b.

| Coating | Coated coil weight before elution (mg) | Coated coil weight after elution (mg) | Drug released (µg) | Drug initial (µg) | % released as shown by coil weight loss during elution | % released as indicated by UV spec. |
|---|---|---|---|---|---|---|
| 1a | 25.775 | 25.183 | 592 | 611 | 97 | 98 |
| 1b | 30.187 | 29.567 | 620 | 633 | 98 | 105 |

As shown in the results, the amount of drug released correlated well with the initial drug weight in the coated composition and with the percent released as indicated by the Elution Assay.

Example 2

In Vitro Release of Triamcinolone Acetonide from Helical Coils

Two different solutions were prepared in tetrahydrofuran (THF) as in Example 1. The compositions prepared are summarized in Table III:

TABLE III

Coating Compositions applied to the Helical Coil.

| Coating | Composition | Parts by weight (pbw) | Weight of coated composition (µg) |
|---|---|---|---|
| Coating 1d | TA/pEVA/pBMA | 50/27.5/22.5 | 1950 |
| Coating 1e | TA/pEVA/pBMA | 50/40/10 | 1928 |

Helical coils with attached caps were fabricated from the alloy MP35N™ (commercially available from ESPI, Ashland, Oreg.). The coils were cleaned in an alkaline solution, then rinsed with deionized water. The coils underwent additional cleaning using an isopropyl alcohol wash and rinse. The coils were dried and weighed prior to coating.

Solutions for Coatings 1d and 1e were sprayed onto the coils using ultrasonic coater equipment that consisted of an ultrasonic spray head (Sono-Tek Milton, N.Y.) and syringe pump system for the coating solution. A pin vise was used to hold the cap of the coil and the coil was held perpendicular to the spray head and rotated. The spray head was moved over the coil to apply the coating composition. The spraying process was continued until the amount of TA on the coils equaled the amount of TA listed for Coatings 1d and 1e listed in Table III. The coating compositions on the helical coil were dried by evaporation of solvent at room temperature (approximately 20° C. to 22° C.). After drying, the coated coils were re-weighed. From this weight, the mass of the coating was calculated, which in turn permitted the mass of the coated polymer(s) and bioactive agent to be determined.

Figure 8:
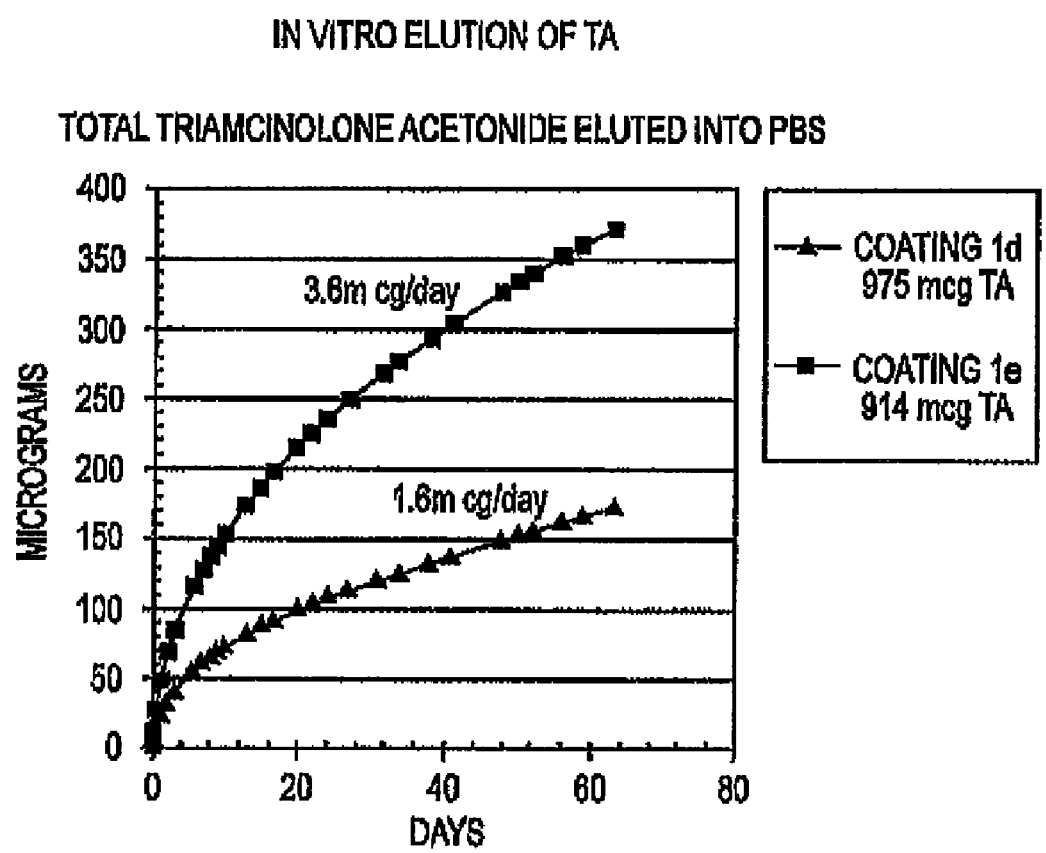
FIG. 8 is a graph showing in vitro elution of triamcinolone acetonide (TA) into phosphate buffered saline (PBS) for the helical coils prepared and tested as described in Example 2.

The coated coils were then subjected to the Elution Assay described above. Results of the Elution Assay for each coating composition are illustrated in FIG. 8.

The release of TA was monitored over 63 days. As shown in FIG. 8, Coating 1d included an initial drug load of 975 µg of TA and approximately 171 µg of the bioactive agent was released within 63 days. Coating 1e included an initial drug load of 914 µg of TA and approximately 371 µg of the bioactive agent was released within 63 days. For coating 1d, the calculated release rate was 1.6 µg/day between days 20 and 63. For coating 1e, the calculated release rate was 3.6 µg/day between days 20 and 63.

Similar to the results discussed in Example I, the elution data for Coatings 1d and 1e indicate that a bioactive agent can be predicted to elute from a coated composition according to the invention for surprisingly long periods of time in vitro. Further, the coating compositions again showed a substantially linear release rate over time (between days 20 and 63). Similar to Example I, results illustrated that the elution rate of the bioactive agent can be controlled by varying the coated composition.

At the conclusion of the Elution Assay, the coils were washed with water, dried, and reweighed. Pre- and post-elution data for coated composition 1d and 1e along with the percent released as indicated by the Elution Assay is provided in Table IV below:

TABLE IV

Elution Data for Coated Composition 1d and 1e.

| Coating | Coated coil weight before elution (mg) | Coated coil weight after elution (mg) | Drug released (µg) | Drug initial (µg) | % released as shown by coil weight loss during elution | % released as indicated by UV spec. |
|---|---|---|---|---|---|---|
| 1d | 32.392 | 32.213 | 179 | 975 | 19 | 18 |
| 1e | 33.204 | 32.817 | 387 | 913.5 | 42 | 41 |

As shown in the results, the percent of drug released as determined by the coil weight before and after elution correlated well with the percent of drug released as determined by UV spectroscopy.

Example 3

In Vivo Release of Triamcinolone Acetonide from Helical Coils

Ten coils were coated with two different formulations, Dose A and Dose B, and were implanted into the vitreous chamber of rabbit eyes to provide sustained release of triamcinolone acetonide. Table V summarizes the coating compositions applied to the coils in this Example. Dose B was designated a "fast release" coating, and this coating composition included a relatively larger ratio of pEVA to PBMA, as compared to the "slow release" Dose A coating composition.

The coating solutions were prepared according to the procedure described in Example I. The coating solutions were applied to the coils according to the procedure described in Example II. The coated coils were implanted into the vitreous chamber of rabbit eyes as follows. The conjunctiva was dissected and pulled away from the incision site, and an incision was made into the eyes utilizing a needle stick through the sclera. A self-starting coil that included a sharp tip was utilized to insert the coil into the vitreous chamber of the eye. The coils were inserted until the cap of the coils abutted the outer surface of the eye, and the conjunctiva was pulled over the cap at the conclusion of the insertion procedure.

Figure 9:
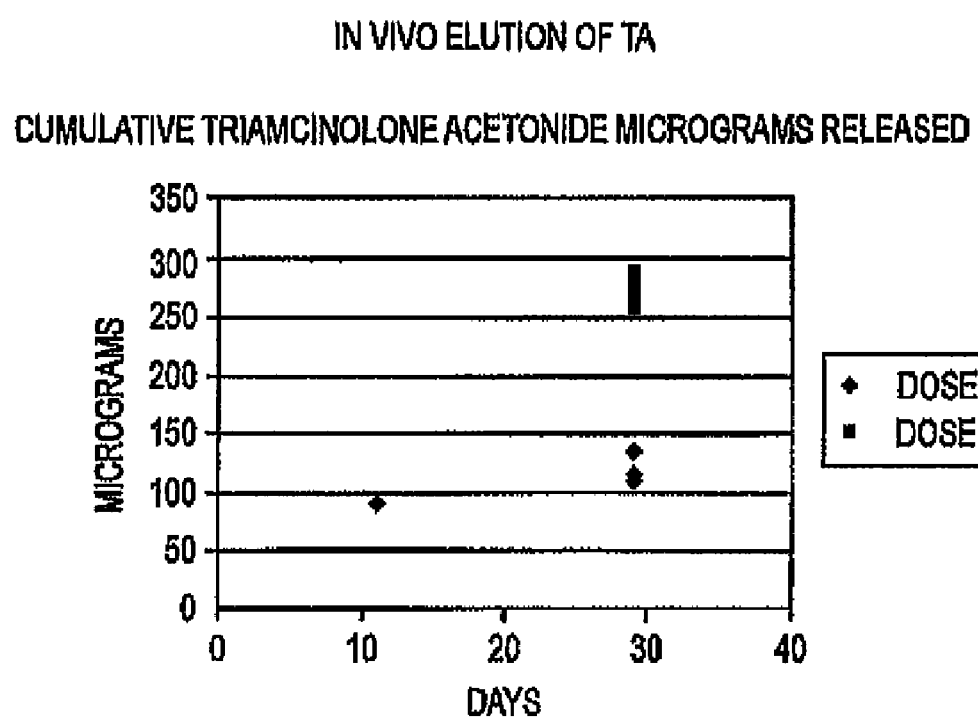
FIG. 9 is a graph showing in vivo elution of triamcinolone acetonide (TA) for the helical coils prepared and tested as described in Example 3.

Five of the Dose B and four of the Dose A coils were implanted for 29 days. One of the Dose A coils was implanted for 11 days. After explantation of the coils, the residual drug within the coated coils was determined. The coatings were dissolved, and the drug and polymer were separated. The HPLC analysis consisted of a C18 column, a gradient elution using acetonitrile and deionized water and UV detection. The results from the solution containing the drug was compared to a calibration curve created from freshly prepared working standards. The amount of drug released was calculated and plotted in FIG. 9.

TABLE V

Coating Composition Applied to the Helical Coil.

| Coil # | Dose Formulation | Coating Formulation | Parts by weight | Weight of TA in the Coated Composition (µg) |
|---|---|---|---|---|
| 1 | A | TA/pEVA/pBMA | 50/10/40 | 950 |
| 2 | A | TA/pEVA/pBMA | 50/10/40 | 936 |
| 3 | A | TA/pEVA/pBMA | 50/10/40 | 1012 |
| 4 | A | TA/pEVA/pBMA | 50/10/40 | 911 |
| 5 | A | TA/pEVA/pBMA | 50/10/40 | 932 |
| 6 | B | TA/pEVA/pBMA | 50/27.5/22.5 | 981 |
| 7 | B | TA/pEVA/pBMA | 50/27.5/22.5 | 974 |
| 8 | B | TA/pEVA/pBMA | 50/27.5/22.5 | 957 |
| 9 | B | TA/pEVA/pBMA | 50/27.5/22.5 | 975 |
| 10 | B | TA/pEVA/pBMA | 50/27.5/22.5 | 965 |

Results indicated the amount of TA released within 11 and 29 days from the Dose A implanted coated coil was approximately 92 and 126 µg, respectively. The amount of TA released within 29 days from the Dose B implanted coil was approximately 275 µg. The amount of TA released from the "fast release" formulation, Dose B, was approximately 2.2 times the amount of TA released from the "slow release" formulation, Dose A.

The implanted materials appeared to be well tolerated by ocular tissue throughout the 29-day follow-up period. No anterior or vitreous chamber inflammation was observed at either the 1-week or 4-week post-operative examination. Similarly, there was no elevation of intraocular pressure or conjunctival thinning associated with the implant.

Following explantation, the Dose A and Dose B coils were observed by 40× magnification light microscopy. No damage (scratches, delamination, or cracks) to the coatings was detected.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

We claim:

1. A controlled release bioactive agent delivery device for treatment of an eye, the device comprising:
    a) a body member having a direction of extension, a longitudinal axis along the direction of extension, and a proximal end and a distal end, wherein at least a portion of the body member deviates from the direction of extension; and
    b) a polymeric coated composition in contact with a surface of the body member to provide a coated surface, the polymeric coated composition comprising a first polymer, a second polymer, and a bioactive agent,
    wherein the first polymer and the second polymer are hydrophobic, and wherein the first polymer comprises polyalkyl(meth)acrylate, aromatic poly(meth)acrylate, or a combination thereof, and wherein the second polymer comprises polyethylene-co-vinyl acetate),
    wherein the body member has a length such that, upon placement of the device at an implantation site within a posterior segment of an eye, the device does not enter a central visual field of the eye, and
    wherein the bioactive agent is present in an amount in the range of 1 µg to 10 mg of bioactive agent per $cm^2$ of the coated surface of the device.

2. The device according to claim 1 wherein the length of the body member is 1 cm or less.

3. The device according to claim 2 wherein the length of the body member is in the range of 0.25 cm to 1 cm.

4. The device according to claim 1 further comprising a cap at the proximal end of the body member.

5. The device according to claim 4 wherein the cap is configured to remain outside the implantation site upon placement of the device at the implantation site.

6. The device according to claim 4 wherein the cap has a thickness of less than 1 mm.

7. The device according to claim 6 wherein the cap has a thickness of less than 0.5 mm.

8. The device according to claim 6 wherein the device has a total length that is less than 1.1 cm.

9. The device according to claim 7 wherein the device has a total length of less than 0.6 cm.

10. The device according to claim 4 wherein the cap has tapered edges.

11. The device according to claim 4 wherein the cap is configured such that it can be sutured to the eye.

12. The device according to claim 4 wherein the dimensions of the device are selected such that, upon placement of the device at an implantation site, the cap is in contact with scleral tissue and conjunctival tissue of the eye, and the body member resides within a vitreous chamber of the eye.

13. The device according to claim 4 wherein the dimensions of the device are selected such that, upon placement of the device at an implantation site, the cap resides within scleral tissue of the eye.

14. The device according to claim 1 wherein the body member is provided with a shape that provides anchoring of the device at the implantation site by requiring manipulation to remove the device from the implantation site.

15. The device according to claim 1 wherein the device is configured for implantation through a pars plana region of the eye.

16. The device according to claim 1 wherein the device is configured for insertion through an incision that is no more than 1 mm in diameter.

17. The device according to claim 16 wherein the device is configured for insertion through an incision that is in the range of 0.25 mm to 1 mm in diameter.

18. The device according to claim 16 wherein the body member is fabricated of a material having an outer diameter that is approximately equal to the diameter of the incision.

19. The device according to claim 18 wherein the body member is formed of a material having a round cross-section.

20. The device according to claim 1 wherein the body member is coil-shaped.

21. The device according to claim 20 wherein the coil-shaped body member includes two or more deviations, and wherein the deviations are spaced from each other a distance of at least 0.5 mm.

22. The device according to claim 1 wherein the distal end of the body member is positioned at the longitudinal axis of the body member.

23. The device according to claim 1 wherein the distal end of the body member is spaced from the longitudinal axis of the body member.

24. The device according to claim 1 wherein the proximal end of the body member is positioned at the longitudinal axis of the body member.

25. The device according to claim 1 wherein the distal end of the body member is configured to pierce the eye during implantation of the device into the eye.

26. The device according to claim 25 wherein the distal end of the body member includes a sharp tip.

27. The device according to claim 26 wherein the distal end of the body member includes a ramp-like angle.

28. The device according to claim 1 wherein the distal end of the body member is rounded.

29. The device according to claim 1 wherein the distal end of the body member is fabricated of a rigid material.

30. The device according to claim 29 wherein the rigid material comprises polyimide.

31. The device according to claim 1 wherein the distal end of the body member is shaped to form a portion that is parallel to the longitudinal axis of the body member.

32. The device according to claim 31 wherein the distal end of the body member includes a rounded tip that is parallel to the longitudinal axis of the body member.

33. The device according to claim 1 wherein the portion of the body member that deviates from the direction of extension includes two or more deviations, and wherein the deviations are spaced from each other a distance of at least 0.5 mm.

\* \* \* \* \*